(12) United States Patent
Mathers et al.

(10) Patent No.: US 8,956,628 B2

(45) **Date of Patent: *Feb. 17, 2015**

(54) BACTERIOPHAGE PREPARATIONS AND METHOD OF USE THEREOF

(75) Inventors: Jeremy J. Mathers, Tinley Park, IL (US); Alexander Sulakvelidze, Towson, MD (US)

(73) Assignee: Zoetis Products LLC, Florham Park, NJ (US)

( * ) Notice: Subject to any disclaimer, the term of this patent is extended or adjusted under 35 U.S.C. 154(b) by 792 days.

This patent is subject to a terminal disclaimer.

(21) Appl. No.: 12/334,863

(22) Filed: Dec. 15, 2008

(65) Prior Publication Data

US 2010/0075398 A1 Mar. 25, 2010

Related U.S. Application Data

(60) Provisional application No. 61/013,325, filed on Dec. 13, 2007.

(51) Int. Cl.

*A61K 39/08* (2006.01)
*C12N 7/00* (2006.01)
*A61K 35/76* (2006.01)

(52) U.S. Cl.

CPC . *C12N 7/00* (2013.01); *A61K 35/76* (2013.01); *C12N 2795/00032* (2013.01); *C12N 2795/00051* (2013.01)

USPC .................................... 424/247.1; 424/203.1

(58) Field of Classification Search

None

See application file for complete search history.

(56) References Cited

U.S. PATENT DOCUMENTS

| | | | |
|---|---|---|---|
| 2,851,006 | A | 9/1958 | Taylor et al. |
| 4,851,240 | A | 7/1989 | Day et al. |
| 5,811,093 | A | 9/1998 | Merril et al. |
| 6,121,036 | A | 9/2000 | Ghanbari et al. |
| 6,461,608 | B1 | 10/2002 | Averback et al. |
| 6,875,431 | B2 | 4/2005 | Fischetti et al. |
| 6,896,882 | B2 | 5/2005 | Ramachandran et al. |
| 6,899,874 | B2 | 5/2005 | Fischetti et al. |
| 6,929,798 | B2 | 8/2005 | Pillich et al. |
| 6,936,244 | B2 | 8/2005 | Fiochetti et al. |
| 6,942,858 | B1 | 9/2005 | Ghanbari et al. |
| 6,955,893 | B2 | 10/2005 | Delisle |
| 7,014,850 | B2 | 3/2006 | Fischetti et al. |
| 7,029,681 | B2 | 4/2006 | Kuo |
| 7,037,506 | B2 | 5/2006 | Kuo |
| 7,087,226 | B2 | 8/2006 | Ramachandran et al. |
| 7,141,241 | B2 | 11/2006 | Fischetti et al. |
| 7,211,426 | B2 | 5/2007 | Bruessow et al. |
| 7,332,307 | B2 | 2/2008 | Carlton et al. |
| 7,459,272 | B2 | 12/2008 | Morris et al. |
| 7,625,739 | B2 * | 12/2009 | Pasternack et al. ........ 435/235.1 |
| 7,625,740 | B2 * | 12/2009 | Pasternack et al. ........ 435/235.1 |
| 2003/0180319 | A1 | 9/2003 | Burden et al. |
| 2004/0219519 | A1 | 11/2004 | Hargis et al. |
| 2005/0136088 | A1 | 6/2005 | Loomis et al. |
| 2005/0153415 | A1 | 7/2005 | Zimmer et al. |
| 2006/0233825 | A1 | 10/2006 | Jayappa et al. |
| 2006/0292135 | A1 | 12/2006 | Loomis et al. |
| 2007/0010001 | A1 | 1/2007 | Bujanover |
| 2007/0020240 | A1 | 1/2007 | Jayasheela et al. |
| 2007/0042357 | A1 | 2/2007 | Miller |
| 2007/0054357 | A1 | 3/2007 | Pasternack et al. |
| 2007/0065547 | A1 | 3/2007 | Coyne et al. |
| 2007/0154459 | A1 | 7/2007 | Hargis et al. |
| 2007/0190033 | A1 | 8/2007 | Soothill et al. |
| 2007/0202088 | A1 | 8/2007 | Baltzley et al. |
| 2007/0212340 | A1 | 9/2007 | Fischetti et al. |
| 2007/0243199 | A1 | 10/2007 | Doelling et al. |
| 2007/0243212 | A1 | 10/2007 | Doelling et al. |
| 2007/0248724 | A1 | 10/2007 | Sulakvelidze et al. |
| 2007/0292397 | A1 | 12/2007 | McNulty et al. |
| 2008/0038322 | A1 | 2/2008 | Murthy et al. |
| 2008/0118468 | A1 | 5/2008 | Sulakvelidze et al. |
| 2008/0194000 | A1 | 8/2008 | Pasternack et al. |
| 2008/0254009 | A1 | 10/2008 | Finegold et al. |
| 2008/0260697 | A1 | 10/2008 | Murthy et al. |
| 2008/0311643 | A1 | 12/2008 | Sulakvelidze et al. |
| 2008/0318311 | A1 | 12/2008 | Murthy et al. |
| 2009/0042754 | A1 | 2/2009 | Okazaki |
| 2009/0047726 | A1 | 2/2009 | Pasternack et al. |
| 2009/0047727 | A1 | 2/2009 | Pasternack et al. |

FOREIGN PATENT DOCUMENTS

| | | | |
|---|---|---|---|
| EP | 0414304 | A2 | 2/1991 |
| GB | 2253859 | A | 9/1992 |
| WO | 2005077046 | A2 | 8/2005 |
| WO | 2006003659 | A2 | 1/2006 |
| WO | 2006047870 | A1 | 5/2006 |
| WO | 2006047871 | A1 | 5/2006 |
| WO | 2006047872 | A1 | 5/2006 |
| WO | 2006125318 | A1 | 11/2006 |
| WO | 2006125319 | A1 | 11/2006 |

OTHER PUBLICATIONS

Markus Zimmer, et al. Genomic analysis of *Clostridium perfringens* bacteriophage 3626 . . . J. Bacteriology 184(16) pp. 4359-4368 (2002).

J.F. Schijven, et al. Bacteriophage and *Clostridium* spores as indicator organisms for removal of pathogens Water Research 37 pp. 2186-2194 (2003).

Smith H Williams, The bacteriophages of *Clostridium perfringens*, J. Gen. Microbiol. 21 pp. 622-630 (1959).

Holzman_"Phage as Antibacterial Tool"; Genetic Engineering News; 18; pp. 1, 12, 41, 48; (1998).

(Continued)

*Primary Examiner* — Jennifer Graser

(74) *Attorney, Agent, or Firm* — G Kenneth Smith

(57) ABSTRACT

Disclosed herein are purified bacteriophage preparations that effectively lyse a plurality of *C. perfringens* strains. In one embodiment, a purified bacteriophage preparation includes four or more *C. perfringens*-specific bacteriophage, wherein each bacteriophage has lytic activity against at least five *C. perfringens* strains. In another embodiment, the purified bacteriophage preparation includes five or more *C. perfringens*-specific bacteriophage.

17 Claims, 6 Drawing Sheets

(56) References Cited

OTHER PUBLICATIONS

Siragusa, et al.; "Lytic Bacteriophage Against *Clostridium perfringens*"; USDA Agricultural Research Service; Technical Abstract; 2 pages; (2004).

Siragusa; "Strategies to Reduce *Clostridium perfringens*"; Presentation Abstract; J. Anim. Sci., 82, Suppl. 1; J. Dairy Sci., 87, Suppl. 1; Poult. Sci., 83, Suppl. 1.; p. 405; (2004).

Intralytix, Inc.; "Veterinary Applications"; www.intralytix.com/Intral_Vet.htm; 2 pages; (2006).

"Bacteriophage Mediated Control of *Clostridium perfringens* in Poultry—LK0642"; Defra—Science Search; pp. 1-2; (2007).

Sharp, et al; "Bacteriophage Mediated Control of *Clostridium perfringens* in Poultry"; Presentation Abstract; BlueMicrobe Viruses—1st VEG Workshop; pp. 1 add 9; Feb. 14-15, 2002.

* cited by examiner

**5.2.1 PFGE analysis of *C. perfringens* chromosomal DNA digested with *SmaI*.**

Lanes 1, 15, 30, 31, 39 and 47 – λ ladder PFGE marker; Lanes 2-14: Cp1-Cp13; Lanes 16-21: Cp14-Cp19; Lanes 22-29: Cp21-Cp28; Lanes 32-38: Cp29-Cp35; Lanes 40-46: Cp36-Cp42.

**Dendrogram portraying the genetic diversity of various *C. perfringens* strains based on *SmaI*-digested PFGE patterns of *C. perfringens* DNA.**

CPLV-42

CPAS-15

CPAS-16

CPTA-37

CPAS-7

BACTERIOPHAGE PREPARATIONS AND METHOD OF USE THEREOF

CROSS REFERENCE TO RELATED APPLICATIONS

This application claims priority to U.S. Provisional Application Ser. No. 61/013,325 filed on Dec. 13, 2007, which is incorporated in its entirety by reference herein.

BACKGROUND

Antibiotic use enhances the growth of healthy domesticated poultry and livestock. Although extensive bans and restrictions have not been implemented in the United States as they have in the E.U. and other countries, pressure for antibiotic alternatives has increased due to concerns of increasing antibiotic resistance among foodborne bacteria. Banning or markedly reducing the agricultural and farm-veterinary use of antibiotics may have a profoundly negative impact on the safety of foods and on the treatment of sick flocks or herds of domesticated livestock, however. Thus, effective, safe, and environmentally friendly alternative(s) to antibiotics are needed to address these concerns and needs.

Viruses that kill bacteria were first identified in the early part of the 20th century by Frederick Twort and Felix d'Herelle who called them bacteriophages or bacteria-eaters (from the Greek phago meaning to eat or to devour). Because of their remarkable antibacterial activity, phages were used to treat diseases of economically important animals/domesticated livestock almost immediately after their discovery, and therapeutic applications for humans closely followed. However, with the advent of antibiotics, phage therapy gradually fell out-of-favor in the United States and Western Europe, and virtually no subsequent research was done on the potential therapeutic applications of phages for bacterial diseases of humans or animals. The emergence of antibiotic-resistance in bacteria, however, has rekindled interest in therapeutic bacteriophages. Phage therapy may have a positive impact on human health by improving the safety of foods in the U.S.A. and elsewhere, and by helping to reduce safely the use of antibiotics in agribusiness.

Among the bacteria that cause significant morbidity and mortality in chickens, *C. perfringens* is one of the most notorious pathogens. In chickens, *C. perfringens* infections are often manifested as necrotic enteritis that occur later in the production cycle, often following a coccidial infection or other insult to the gastrointestinal tract. It is thus desirable to develop bacteriophage preparations suitable to reduce morbidity and mortality in chickens.

SUMMARY

Disclosed herein are purified bacteriophage preparations that effectively lyse a plurality of *C. perfringens* strains. In one embodiment, a purified bacteriophage preparation comprises four or more *C. perfringens*-specific bacteriophage, wherein each bacteriophage has lytic activity against at least five *C. perfringens* strains. In another embodiment, the purified bacteriophage preparation comprises five or more *C. perfringens*-specific bacteriophage.

In another embodiment, a method of reducing chicken mortality due to *C. perfringens* infection comprises administering a purified bacteriophage preparation comprising four or more *C. perfringens*-specific bacteriophage, wherein each bacteriophage has lytic activity against at least five *C. perfringens* strains.

In another embodiment, a method of selecting a *C. perfringens* host strain suitable to propagate bacteriophage from a plurality of test strains comprises microbiologically confirming one test strain from the plurality of test strains as a *C. perfringens* species to produce a confirmed strain; associating the confirmed strain with a poultry disease to produce a disease-associated strain; and applying one or more additional selective criterion to the disease-associated strain selected from minimal antibiotic resistance and absence of animal-virulence markers other than those for *C. perfringens* to produce the *C. perfringens* host strain suitable to propagate bacteriophage.

In yet another embodiment, a method of producing a bacteriophage cocktail comprises mixing four or more *C. perfringens*-specific bacteriophage, wherein each bacteriophage has lytic activity against at least five *C. perfringens* strains.

Figure 1:
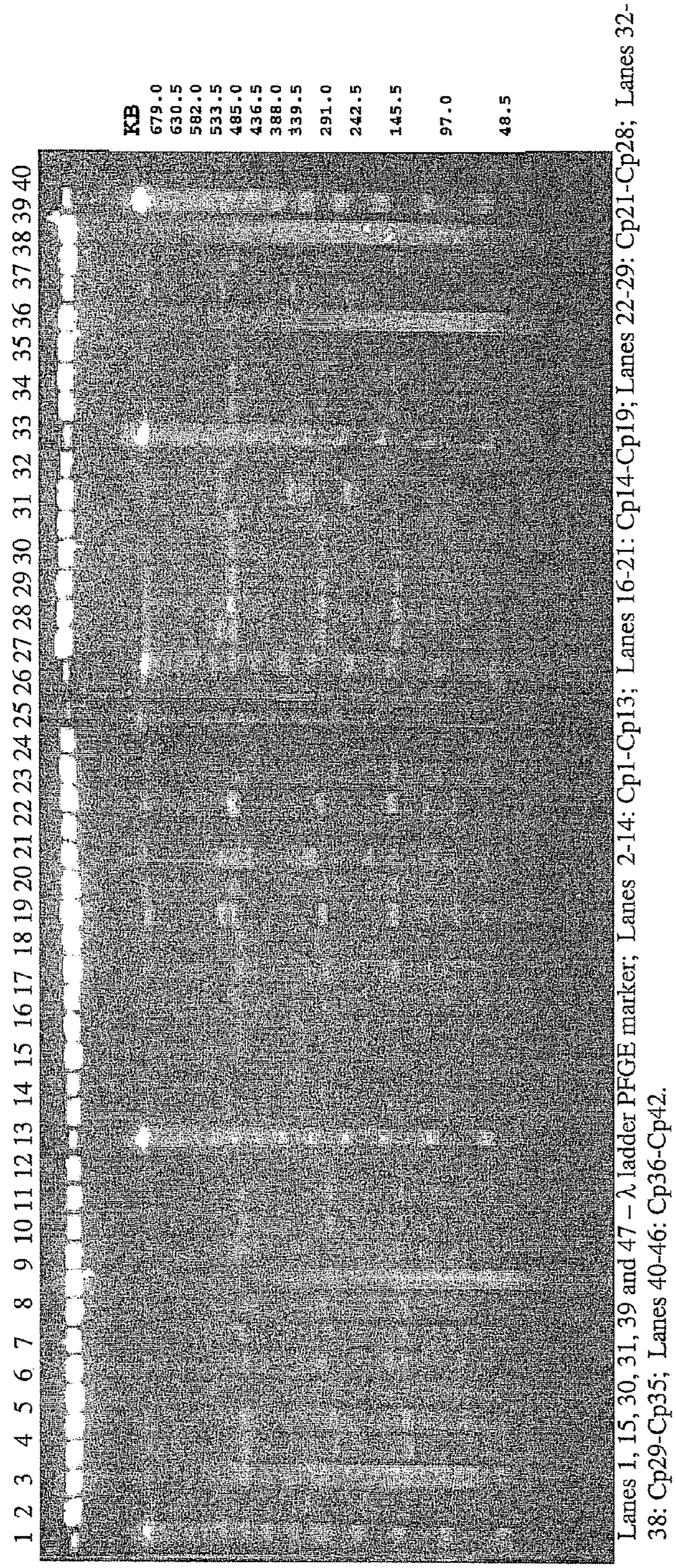
FIG. 1 shows a phylogenetic analysis of *C. perfringens* strains.

The above-described and other features will be appreciated and understood by those skilled in the art from the following detailed description, drawings, and appended claims.

DETAILED DESCRIPTION

Disclosed herein are purified bacteriophage preparations that effectively lyse a plurality of *C. perfringens* strains. Lysis of particular strains is demonstrated by the drop-on-lawn method, which is standard in the art. The bacteriophage preparations are suitable to reduce morbidity and mortality in chickens.

In one embodiment, a purified bacteriophage preparation comprises four or more *C. perfringens*-specific bacteriophage, wherein each bacteriophage has lytic activity against at least five *C. perfringens* strains. In another embodiment, the purified bacteriophage preparation comprises five or more *C. perfringens*-specific bacteriophage.

In one specific embodiment, the bacteriophage preparation comprises CPAS-12 (accession number PTA-8479), CPAS-15 (accession number PTA-8480), CPAS-16 (accession number PTA-8481) and CPLV-42 (accession number PTA-8483). In another embodiment, the bacteriophage preparation consists essentially of CPAS-12, CPAS-15, CPAS-16 and CPLV-42. In yet another embodiment, the bacteriophage preparation consists of CPAS-12, CPAS-15, CPAS-16 and CPLV-42.

In another specific embodiment, the bacteriophage preparation comprises CPAS-7 (accession number PTA-8478), CPAS-12, CPAS-15, CPAS-16 and CPLV-42. In another embodiment, the bacteriophage preparation consists essentially of CPAS-7, CPAS-12, CPAS-15, CPAS-16 and CPLV-42. In yet another embodiment, the bacteriophage preparation consists of CPAS-7, CPAS-12, CPAS-15, CPAS-16 and CPLV-42.

In one embodiment, the *C. perfringens* strains are ATCC strain 25768, ATCC strain 3624, ATCC strain 9856, ATCC strain 3628, ATCC strain 13124, ATCC strain PTA-8495, NRRL strain B-50143, NRRL strain B-50144, NRRL strain B-50145, and combinations comprising one or more of the foregoing strains. In a specific embodiment, the at least five *C. perfringens* strains comprise ATCC strain 3624 and ATCC strain 9856.

In one embodiment, the bacteriophage preparations are characterized by their specificity and effectiveness against *C. perfringens* strains. In one embodiment, the purified bacteriophage preparation lyses greater than or equal to 85% of at least 40 screened *C. perfringens* strains, wherein the bacteriophage preparation is incapable of infecting at least 10 strains of *E. coli, L. monocytogenes, S. enterica*, and *P. aeruginosa*. In another embodiment, the purified bacteriophage preparation lyses greater than or equal to 85% of at least 45 screened *C. perfringens* strains. In yet another embodiment, each of the individual *C. perfringens*-specific bacteriophage lyses 15% to 90% of the screened *C. perfringens* strains.

The term "purified" in reference to a bacteriophage or bacteriophage preparation does not require absolute purity (such as a homogeneous preparation). Instead, it is an indication that the bacteriophage or bacteriophage preparation is relatively more pure than in the natural environment (compared to the natural level, this level should be at least 2-5 fold greater, e.g., in terms of mg/mL). Purification is according to any method known to those of ordinary skill in the art that will result in a preparation of bacteriophage substantially free from other nucleic acids, proteins, carbohydrates, lipids, or subcellular organelles. Individual bacteriophage may be purified to electrophoretic homogeneity. Purification of at least one order of magnitude, preferably two or three orders, and more preferably four or five orders of magnitude is expressly contemplated.

Purity of phage stocks can be deter mined by pulsed-field gel electrophoresis (PFGE) of uncut DNA. In one embodiment, approximately 100-200 ng of the phage DNA is electrophoresed in a 1% SeaKem Gold Agarose (Cambrex, Rockland, Me.) gel with 0.5× Sodium boric acid (1×SB: 10 mM sodium hydroxide pH adjusted to 8.5 with boric acid) buffer at 14° C. in a CHEF Mapper XA PFGE apparatus (Bio-Rad Laboratories, Hercules, Calif.). The run time is 12 hours with a voltage of 6 V/cm and a linearly ramped pulse time of 0.06 s to 8.53 seconds. The gels ware stained with ethidium bromide and visualized with UV light.

In one embodiment, endotoxin levels for lots of phage produced are determined by a *Limulus* amoebocyte lysate (LAL) assay using a chromogenic assay (QCL-1000 Kit, BioWhittaker, Walkersville, Md.) following the manufacturers' recommendations. A standard curve with *E. coli* endotoxin (supplied with kit) ranging from 0.1 to 1.0 endotoxin units (EU) per milliliter endotoxin is constructed for each assay by plotting the optical density at 405 nm ($OD_{405}$) versus EU/ml. Phage samples are assayed diluted in sterile water (USP, Baxter, Deerfield, Ill.) and the absorbance at 405 nm was measured with a μQuant (Bio-Tek Instruments, Inc., Winooski, Vt.) microplate reader. Endotoxin concentrations for each sample are calculated by linear regression from the standard curve.a Standards and samples are analyzed in triplicate.

In one embodiment, carbohydrate content for all lots of phage produced is determined by an anthrone method. A standard curve with glucose ranging from 10 to 250 μg/ml is constructed for each assay by plotting the optical density at 625 nm ($OD_{625}$) versus μg/ml of glucose concentration. Phage samples are assayed in PBS and the absorbance at 625 nm is measured with a μQuant (Bio-Tek Instruments, Inc.) microplate reader. Carbohydrate concentrations for each sample are calculated by linear regression from the standard curve. Standards and samples are analyzed in duplicate.

In one embodiment, the total protein content for lots of phage produced is determined by a bicinchoninic acid (BCA) assay using a colorimetric assay (BCA™ Protein Assay Kit, Pierce, Rockford, Ill.) following the manufacturers' recommendations. A standard curve with bovine serum albumin (BSA, supplied with kit) ranging from 20 to 2,000 μg/ml protein is constructed for each assay by plotting the optical density at 562 nm ($OD_{562}$) versus μg/ml BSA. The absorbance at 562 nm is measured with a μQuant (Bio-Tek Instruments, Inc.) microplate reader. Total protein concentrations for each sample are calculated by linear regression from the standard curve. Standards and samples are analyzed in triplicate.

The term "strain" means bacteria or bacteriophage having a particular genetic content. The genetic content includes genomic content as well as recombinant vectors. Thus, for example, two otherwise identical bacterial cells would represent different strains if each contained a vector, e.g., a plasmid, with different phage open reading frame inserts.

By "treatment" or "treating" is meant administering a bacteriophage preparation for prophylactic and/or therapeutic purposes. The term "prophylactic treatment" refers to treating an animal that is not yet infected but is susceptible to or otherwise at risk of a bacterial infection. The term "therapeutic treatment" refers to administering treatment to an animal already suffering from infection.

The term "bacterial infection" means the invasion of the host organism, animal or plant, by pathogenic bacteria. This includes the excessive growth of bacteria which are normally present in or on the body of the organism, but more generally, a bacterial infection is any situation in which the presence of a bacterial population(s) is damaging to a host organism. Thus, for example, an organism suffers from a bacterial infection when excessive numbers of a bacterial population are present in or on the organism's body, or when the effects of the presence of a bacterial population(s) is damaging to the cells, tissue, or organs of the organism.

The terms "administer", "administering", and "administration" refer to a method of giving a dosage of a bacteriophage preparation to an organism. Suitable methods include topical, oral, intravenous, transdermal, intraperitoneal, intramuscular, or intrathecal. The preferred method of administration varies depending on various factors, e.g., the components of the bacteriophage preparation, the site of the potential or actual bacterial infection, the bacterium involved, and the infection severity.

In the context of treating a bacterial infection a "therapeutically effective amount" or "pharmaceutically effective amount" indicates an amount of a bacteriophage preparation which has a therapeutic effect. This generally refers to the inhibition, to some extent, of the normal cellular functioning of bacterial cells that render or contribute to bacterial infection.

The dose of bacteriophage preparation that is useful as a treatment is a "therapeutically effective amount". Thus, as used herein, a therapeutically effective amount means an amount of a bacteriophage preparation that produces the desired therapeutic effect as judged by clinical trial results. This amount can be routinely determined by one skilled in the art and will vary depending on several factors, such as the particular bacterial strain involved and the particular bacteriophage preparation used.

In one embodiment, a bacteriophage preparation optionally includes one or more pharmaceutically acceptable excipients. In one embodiment, the excipient is a water-conditioning agent, for example agents suitable for water dechlorination and/or phage stabilization. Such agents are innocuous to the bacteriophage cocktail, but when added prior to or simultaneously with *C. perfringens* bacteriophage or bacteriophage cocktails, act to dechlorinate municipal levels of chlorine, which if untreated would kill or significantly reduce the viability of the bacteriophage or bacteriophage cocktail. Exemplary water-conditioning agents include amino acids and/or salts which help to normalize the pH and ionic balance of the bacteriophage cocktail, when added to diverse water sources used for the animal's drinking and for phage delivery. In one embodiment, the water-conditioning agent is a 50 mM citrate-phosphate-thiosulfate (CPT) buffer, comprising about 40 mg sodium thiosulfate, 6.0 gm disodium phosphate (anhydrous), 1.1 gm citric acid (anhydrous) per liter of deionized water, pH 7.0. By including water-conditioning agents in the cocktail or adding separately to the treatment water, the water-conditioning agents act to both stabilize and protect the bacteriophage cocktail in a commercial preparation suitable for routine field use.

A method of producing a bacteriophage cocktail comprises mixing four or more *C. perfringens*-specific bacteriophage, wherein each bacteriophage has lytic activity against at least 5 *C. perfringens* strains. In another embodiment, a method of producing a bacteriophage cocktail comprises mixing five or more *C. perfringens*-specific bacteriophage, wherein each bacteriophage has lytic activity against at least 5 *C. perfringens* strains Once *C. perfringens* cocktail have been selected, further testing can be employed to refine the specificity of the cocktail. In one embodiment, a bacteriophage cocktail is tested against additional *C. perfringens* strains which have antibiotic resistance genes to test the phage cocktail against antibiotic-resistant strains and evaluate the cocktail's potential for use in the field against antibiotic-resistant Clostridia. In another embodiment, a bacteriophage cocktail is tested against *C. perfringens* strains derived from animal species other than chickens to further evaluate and define the host range of the strain or strains to include additional animal species (e.g., swine, cattle, turkey, sheep, exotics, dogs, cats, and the like) In another embodiment, a bacteriophage cocktail is tested against *Clostridium* of different species (i.e., other than *C. perfringens*), which will further define the range of effectiveness of the phage cocktail. In yet another embodiment, a bacteriophage cocktail is tested against additional gram-positive bacteria (e.g., both reference strains and animal-associated types, aerobic and anaerobic) to further evaluate and define host range. In another embodiment, a bacteriophage cocktail is tested against additional gram-negative and gram-variable microorganisms to further evaluate host range. In another embodiment, a bacteriophage cocktail is tested for pre-conditioning or additive formulations, using different levels of stabilizing and dechlorinating water-conditioning agents, for optimally maintaining the viability of the phage cocktail under a wide range of water types and chlorination levels as may be expected in field usage conditions.

In another embodiment, the method further comprises testing the potential of the bacteriophage cocktail for the development of intrinsic phage resistance in the target host. Testing includes challenging test *C. perfringens* host strains with individual and/or combined bacteriophage cocktail phage over several cycles, and ascertaining the rate of resistance development toward the individual phages as well as that of the combination(s) of phages. It is anticipated that the combination bacteriophage cocktail will have significantly less development of resistance against a given individual host strain. An optimum combination of bacteriophages may be further elucidated using known mathematical optimization techniques or software packages (Box-Hunter, Latin Squares, Taguchi, Simplex, etc.) as applied to the bacteriophage resistance data generated from such experimentation.

Advantages of bacteriophage therapy include high bactericial activity, high selectivity permitting targeting of specific pathogens while leaving desirable bacterial flora intact, specificity for prokaryotic cells, and environmental benignity. In livestock and poultry applications, bacteriophage have the advantage of specificity that should not select for phage-resistance in non-target bacterial species, the possible emergence of resistance against phages will not affect the susceptibility of the bacteria to antibiotics used to treat humans, and, unlike antibiotics, phage preparations can readily be modified in response to changes in bacterial pathogen populations or susceptibility.

The poultry and livestock industries use antibiotics for three main purposes: (i) prophylactically, to prevent disease in flocks, herds, etc., (ii) to treat sick livestock, and (iii) to improve digestion and utilization of feed, which often results in improved weight gain. Antibiotics used in the latter setting often are referred to as "growth-promoting antibiotics" or GPAs. Most GPAs are not commonly used in human medicine, and they are usually administered, in small amounts, to poultry and other livestock via food. Bacteriophages can effectively replace and/or reduce the use of antibiotics in all three of the above-mentioned settings.

Among the bacteria that cause significant morbidity and mortality in chickens, *C. perfringens* is one of the most notorious pathogens. In order to identify effective bacteriophage for a genetically diverse population of *C. perfringens* strains, isolates of *C. perfringens* were first identified. In order to identify effective bacteriophage, it is useful to identify *C. perfringens* strains that affect poultry at various locations within the United States. As shown herein, forty-one strains of *C. perfringens* were isolated from various sources and characterized by pulsed-field gel electrophoresis (PFGE) typing. (FIG. 1) Among the 35 strains subjected to PFGE, phylogenetic analysis showed that these strains clustered into 15 heterogenic groups. (FIG. 2) Among these 15 PFGE types, P6 is the predominant type (10 strains) followed by P4 (6 strains). Additional *C. perfringens* strains may be obtained from publicly available collections.

One important factor in the identification of bacteriophage is the selection of *C. perfringens* strains suitable for their identification. In one embodiment, a method of selecting a *C. perfringens* host strain suitable to propagate bacteriophage from a plurality of test strains, comprises microbiologically confirming one test strain from the plurality of test strains as a *C. perfringens* species to produce a confirmed strain; associating the confirmed strain with a poultry disease to produce a disease-associated strain; applying one or more additional selective criterion to the disease-associated strain selected from minimal antibiotic resistance and absence of animal-virulence markers other than those for *C. perfringens* to produce the *C. perfringens* host strain suitable to propagate bacteriophage. In one embodiment, the selection criterion is minimal antibiotic resistance and the antibiotic resistance is tetracycline, ampicillin, tylosin, erythromycin, lincomycin, chloramphenicol or other drug resistance. The selection of strains absent from antibiotic resistance minimizes the potential transduction of plasmid or chromosomal-borne antibiotic resistance genes, into the subsequent bacteriophage cocktail genomes. The advantage of this applied criterion, is to in advance, limit any potential resistance genes in a bacteriophage cocktail preparation. The selective criterion used for these phage cocktail host strains, are a unique extension of a unique library of *C. perfringens* strains, combined with microbiological knowledge of antibiotic resistance, along with skills in running antibiotic susceptibility tests to ascertain the resistance profiles of the submitted host strains.

Six novel bacteriophages of the Siphoviridae or Myoviridae families that infect *Clostridium perfringens* were isolated from environmental water or sewage sources. Phage are characterized, for example, at both the protein and nucleic acid level. The optimal host strain for propagation of each bacteriophage is identified and all phage are preferably negative for endogenous phage. In addition, each bacteriophage is characterized by PFGE, RAPD, SDS-PAGE, and other approaches. Stocks of all six monophages and their respective host strains are made for use in characterization and production of each phage.

The *C. perfringens*-specific monophages are capable of specifically infecting *C. perfringens* strains, and are not capable of infecting/growing on *E. coli, L. monocytogenes, S. enterica*, and *P. aeruginosa*. As used herein, the teen *C. perfringens*-specific refers to bacteriophage and bacteriophage preparations that are capable of infecting a plurality of *C. perfringens* strains and are incapable of infecting at least 10 strains of *E. coli, L. monocytogenes, S. enterica*, and *P. aeruginosa.*

Six bacteriophages that infect *Clostridium perfringens* are sequenced. (SEQ ID NOs:1-6) Five of the six phages are sequenced, and each predicted open reading frame is identified in each genome. Each of the predicted genes was annotated. None of the 17 undesirable genes (Table 5.1.1) is found in the genomes of any of the five phages for which sequences were available.

Two phage cocktails, INT-401 (CPAS-7, CPAS-12, CPAS-15, CPAS-16, and CPLV-42) and INT-402 (CPAS-12, CPAS-15, CPAS-16, CPLV-42), are prepared from five of the six monophages isolated. Both cocktails are effective in killing greater than 85% of the 46 *C. perfringens* strains screened. INT-401 was selected for use in proof-of-principle efficacy studies designed to determine the prevention of necrotic enteritis in *C. perfringens* challenged broiler chickens.

Oral Gavage of Test Article (INT-401 phage cocktail) to birds on the day of challenge (Day 14) and for the next four days significantly reduced mortality due to NE. Growth performance in this group was numerically equivalent to the non-challenged control, and appeared to be better compared to the challenged, but phage-untreated chickens. Given the fact that many chickens are naturally colonized with *C. perfringens*, the latter observation warrants further elucidation, to better examine the possible growth performance-enhancing benefits of the phage preparation.

Two of the three "in ovo" treatments had numerically reduced NE mortality (9.6 and 14.8%) when compared to the Challenged control (25.9%).

Oral Gavage of Test Article prior to challenge, or spray of Test Article to chicks at the hatchery, was ineffective in preventing NE mortality due to *C. perfringens* challenge.

The results of the studies herein suggest that *C. perfringens*-specific phage preparation can be effective in significantly reducing chicken mortality due to *C. perfringens* infections in chickens such as those causing necrotic enteritis when administered shortly after the bacterial challenge. Further dosing- and delivery-optimization studies are warranted, together with further fine-tuning of the product for the optimal efficacy.

Exemplary means of administration of the bacteriophage preparations are oral administration, intramuscular injection, subcutaneous injection, intravenous injection, intraperitoneal injection, eye drop, nasal spray, and the like. When the subject to be treated is a bird, the bird may be a hatched bird, including a newly hatched (i.e., about the first three days after hatch), adolescent, and adult birds. Birds may be administered the vaccine in ovo, as described in U.S. Pat. No. 4,458,630 to Sharma, for example, incorporated herein by reference.

In one embodiment, the bacteriophage preparation is administered in an animal feed such as poultry feed. The bacteriophage preparation is prepared in a number of ways. For instance, it can be prepared simply by mixing the different appropriate compounds to produce the bacteriophage preparation. The resulting bacteriophage preparation can then be either mixed directly with a feed, or more conventionally impregnated onto a cereal-based carrier material such as milled wheat, maize or soya flour. Such an impregnated carrier constitutes a feed additive, for example.

The bacteriophage preparation may be mixed directly with the animal feed, or alternatively mixed with one or more other feed additives such as a vitamin feed additive, a mineral feed additive or an amino acid feed additive. The resulting feed additive including several different types of components can then be mixed in an appropriate amount with the feed. It is also possible to include the bacteriophage preparation in the animal's diet by incorporating it into a second (and different) feed or drinking water which the animal also has access to. Accordingly, it is not essential that the bacteriophage preparation is incorporated into the usual cereal-based main feed of an animal.

In one embodiment, included are methods of identifying an optimized field delivery modes and conditions for phage cocktail applications. In one embodiment, an optimized administration condition is water administration, for up to 3 days at temperatures up to 50° C.

The bacteriophage preparation can be used for a wide variety of animals, but use of the bacteriophage preparation is particularly preferred in domestic animals and farm livestock. Animals which may in particular benefit from the bacteriophage preparation include poultry (such as chickens, turkeys, ducks and geese), ruminants (such as cattle, horses and sheep), swine (pigs), rodents (such as rabbits) and fish. The bacteriophage preparation is particularly useful in broiler chickens.

The invention is further illustrated by the following non-limiting examples.

EXAMPLES

Example 1

Characterization of *Clostridium perfringens* Isolates

Media: Brain Heart Infusion (BHI) broth or BHI agar was used to grow all isolates. All media were obtained from EMD Chemicals, Gibbstown, N.J.

Microorganisms: Forty-two *C. perfringens* strains were employed. One strain (Cp 20) did not grow and was excluded from further analysis. As part of the collection process, isolates were checked for purity and frozen at −80° C. in 30% glycerol. Most of the work was performed in an anaerobic chamber (Plas-Labs, Inc. Lansing, Mich.), that contained a 90% $N_2$-5% $H_2$-5% $CO_2$ atmosphere.

Bacteriophage: All bacteriophages were isolated from environmental water sources.

Phage Isolation: Samples of water collected for the isolation of phage were mixed with 10×BHI broth, inoculated with a single *C. perfringens* strain of interest and incubated anaerobically at 37° C. overnight. The samples were centrifuged (8,000×g, 10 min) to remove the bacterial cells and sterile filtered (0.22 µm Stericup™, Millipore, Bedford, Mass.). Filtrates were serially diluted in BHI broth and titered using the soft-agar overlay method. Briefly, dilutions of each filtrate were mixed with log-phase bacterial culture, incubated at 37° C. for 10 minutes, molten soft-agar added, poured onto BHI agar plates and incubated anaerobically at 37° C. overnight. Individual plaques were picked from the overlay plates and titered a second time as an initial step in ensuring that each phage was pure.

Screening for Endogenous Phage: *Clostridium perfringens* strains used for propagating the phages were screened for endogenous bacteriophage by the drop on lawn method. Liquid cultures of the host strains were grown overnight, centrifuged (9,500×g, 5 minutes) to remove the bacteria and filtered through a 0.22 µm syringe filter (Millipore). The same strains were grown in BHI broth to an $OD_{600}$ of 0.1-0.3. Two hundred microliters of each screening strain was mixed with molten soft-agar and poured onto a BHI agar plate. After the soft-agar hardened 10 µl of each host strain filtrate was spotted onto the plates with the screening strains. Lytic activity was observed after overnight anaerobic incubation at 37° C.

*Clostridium perfringens* Host Strain Typing: The 41 *C. perfringens* strains received were typed by PFGE using the National Molecular Subtyping Network (PulseNet) standard protocol. *Clostridium perfringens* strains were grown on BHI agar overnight anaerobically at 37° C. and suspended in 75 mM NaCl-25 mM EDTA (pH 8.0) (CSB) buffer to an $OD_{610}$ of 1.3-1.4. The bacterial cells were embedded in 1.2% SeaKem® Gold Agarose (Cambrex, Rockland, Me.) by mixing equal volumes (0.4 mL) of the cell suspension and melted agarose made in TE buffer. Plugs were made in 1.5-mm thick molds (Bio-Rad Laboratories, Hercules, Calif.) and solidified at 4° C. The cells were lysed by incubation in lysis buffer (50 mM Tris-HCl [pH 8.0], 50 mM EDTA [pH 8.0], 1% N-laurylsarcosine, and proteinase K [1 mg/ml]) at 55° C. overnight. The plugs were washed at 54° C. with shaking three times for 15 minutes each in sterile water and then three times in TE buffer. The plugs were stored at 4° C. in TE buffer.

Plugs were equilibrated with restriction endonuclease buffer at 25° C. overnight. The plugs were digested with SmaI (New England Biolabs, Beverly, Mass.) according to the manufacturers' recommendations overnight. Restriction fragments were separated by electrophoresis through a 1% agarose gel in 0.5× Tris-borate-EDTA (10× TBE, EMD Chemicals) with 1 mM thio-urea at 14° C. in a CHEF Mapper XA PFGE apparatus (Bio-Rad Laboratories). The run time was 20 hours with a voltage of 6 V/cm and a linearly ramped pulse time of 0.4 seconds to 40 seconds. The size range analyzed was 40-1,400 kilobases.

Data Handling & Analysis: A large zone of clearing (lytic activity) produced on lawns of any of the *C. perfringens* strains where the culture filtrate was applied were considered positive for endogenous phage.

Host Strain Typing: Analysis of the PFGE banding patterns was done with Quantity One (ver. 4.41) and Molecular Analyst Fingerprinting (ver. 1.6) software (Bio-Rad Laboratories) to determine the genetic relatedness of the strains. The dendrogram was constructed by the UPGMA algorithm with a 4% tolerance for fragment shifts. Isolates were considered closely related if their PFGE patterns differed by less than three fragments when digested with the restriction endonuclease SmaI.

PFGE Results: Forty-one strains of *C. perfringens* were isolated from various sources and characterized by pulsed-field gel electrophoresis (PFGE) typing. (Table 1) Among the 35 strains (one strain did not grow and six were not type-able due to nuclease problems) subjected to PFGE, phylogenetic analysis showed that these strains clustered into 15 heterogenic groups. (FIG. 1) Among these 15 PFGE types, P6 is the predominant type (10 strains) followed by P4 (6 strains). *C. perfringens* strain Cp27 has ATCC accession number PTA-8495.

TABLE 1

*Clostridium perfringens* isolates

| Intralytix ID | Alpharma ID[a] | Isolation Year | Source | Location | Pathogenic (Yes/No) | Comment | PFGE Type |
|---|---|---|---|---|---|---|---|
| Cp 1 | 7998 B | 1995 | Roney | Canada | Yes | | P1 |
| Cp 2 | UAZ 75 | — | — | — | — | | P2 |
| Cp 3 | Wallers | 1993 | — | IL | Yes | | P3 |
| Cp 4 | Pennington | 1993 | — | IL | Yes | | P4 |
| Cp 5 | 96-7413 | 1996 | Roney | AL | Yes | | NT |
| Cp 6 | UAZ 74 | — | — | — | — | | P5 |
| Cp 7 | Warren | 1993 | — | IL | Yes | | P6 |
| Cp 8 | AU1 | 1996 | — | AL | Yes | Gangrenous Dermatitis | P7 |
| Cp 9 | 95-949 | 1995 | Fitz-Coy | East Coast | Yes | | NT |
| Cp 10 | M1 | 2000 | Fitz-Coy | East Coast | Yes | | P8 |
| Cp 11 | Harmes | 1993 | — | IL | Yes | | P3 |
| Cp 12 | 94-5223 | 1994 | Thayer | GA | Yes | | P6 |
| Cp 13 | D00-20250 | 2000 | Fitz-Coy | MN | Yes | | NT |
| Cp 14 | UDE 95-1377 | 1995 | Fitz-Coy | DE | Yes | | P9 |
| Cp 15 | 95-1046 | 1995 | Fitz-Coy | DE | Yes | Gall Bladder | NT |
| Cp 16 | F96-01993 | 1996 | Fitz-Coy | CA | Yes | | P6 |
| Cp 17 | UAZ 257 | — | — | — | — | | P10 |
| Cp 18 | 94-5228 | 1994 | Thayer | GA | Yes | | P11 |
| Cp 19 | Gresbrecht A | 1993 | — | IL | Yes | | P6 |
| Cp 20 | 96-2873 | 1996 | Roney | AL | Yes | Did not grow | * |

TABLE 1-continued

*Clostridium perfringens* isolates

| Intralytix ID | Alpharma ID[a] | Isolation Year | Source | Location | Pathogenic (Yes/No) | Comment | PFGE Type |
|---|---|---|---|---|---|---|---|
| Cp 21 | URZ298 | — | — | — | — | | P12 |
| Cp 22 | FC1 | 1995 | Fitz-Coy | East Coast | Yes | | P13 |
| Cp 23 | Kendall | 1993 | — | IL | Yes | | P4 |
| Cp 24 | UDE 95-1372 | 1995 | Fitz-Coy | DE | Yes | | P14 |
| Cp 25 | C97M3 | 1997 | — | CO | Yes | | P4 |
| Cp 26 | Reed | 1993 | — | IL | Yes | | P4 |
| Cp 27 | AU2 | 1996 | Roney | AL | Yes | Gangrenous Dermatitis | P7 |
| Cp 28 | A1A | 2002 | Skinner | DE | Yes | | P15 |
| Cp 29 | 96-7414 | 1996 | Roney | AL | Yes | | P13 |
| Cp 30 | 94-5230 | 1994 | Thayer | GA | Yes | | P6 |
| Cp 31 | 94-5224 | 1994 | Thayer | GA | Yes | | P6 |
| Cp 32 | FC2 | 1995 | Fitz-Coy | East Coast | Yes | | P4 |
| Cp 33 | 94-5229 | 1994 | Thayer | GA | Yes | | P6 |
| Cp 34 | 7998C | 1995 | — | Canada | Yes | | P1 |
| Cp 35 | S1-1 | 2000 | Fitz-Coy | East Coast | Yes | | P6 |
| Cp 36 | 94-5227 | 1994 | Thayer | GA | Yes | | P6 |
| Cp 37 | Jones | 1993 | — | IL | Yes | | P6 |
| Cp 38 | 6A | 2002 | Skinner | NJ | Yes | | P14 |
| Cp 39 | S1-7 | 2000 | Fitz-Coy | East Coast | Yes | | NT |
| Cp 40 | 7998A | 1995 | Roney | Canada | Yes | | P1 |
| Cp 41 | 95-1000 | 1995 | Fitz-Coy | — | — | | P4 |
| Cp 42 | AU3 | 1996 | Roney | — | — | | NT |

* Isolate failed to grow.
NT = Not Typed.

All isolates were from intestines unless otherwise noted. All isolates were of chicken origin.

Figure 2:
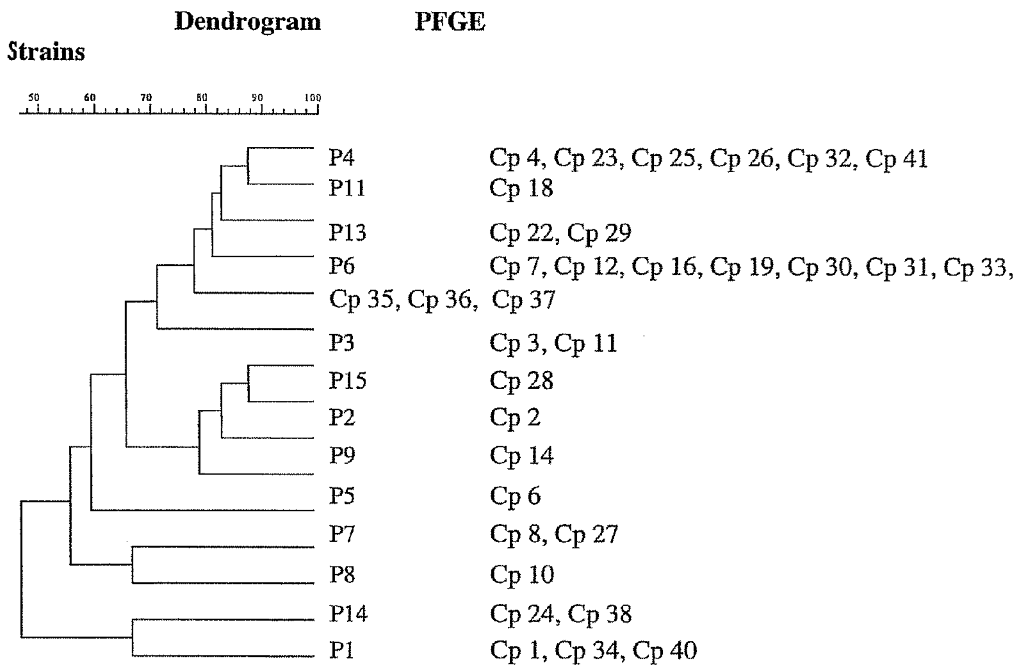
FIG. 2 is a dendrogram portraying the genetic diversity of various *C. perfringens* strains based on SmaI-digested PFGE patterns of *C. perfringens* DNA.
Figure 3:
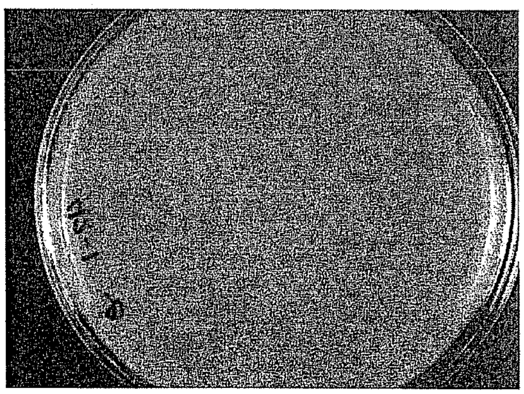
FIG. 3 shows phage plaques produced by representative bacteriophage infecting *C. perfringens* strain Cp 42.

A dendrogram portraying the genetic diversity of various *C. perfringens* strains based on SmaI-digested PFGE patterns of *C. perfringens* DNA is shown in FIG. 2. Among the strains making up the 15 PFGE types, 16 strains (about 46%) were grouped in PFGE types P6 (10 strains) and P4 (6 strains). The remaining 20 strains clustered into eight PFGE types represented by a single strain (PFGE types P2, P5, P8, P9, P10, P11, P12 and P15), four PFGE types represented by two strains each (PFGE types P3, P7, P13 and P14), and one PFGE type represented by three strains (PFGE type P1). While some of the strains within the same PFGE type were associated with the same geographic location/source/year of isolation (e.g., both strains in PFGE type P3 have come from the Illinois Disease Lab, and they both were isolated in 1995), the number of strains in the PFGE types other than P4 and P6 was too small for making generalized conclusions about their specific association with any given facility/location. Strains in the PFGE types P4 and P6 did not appear to be associated with a specific geographic location/source of isolation (e.g., strains in the PFGE type P6 were isolated from various sources in Illinois, Georgia and California). FIG. 3 shows phage plaques produced by representative bacteriophage infecting *C. perfringens* strain Cp 42.

In sum, four to six candidate bacteriophages lytic for *C. perfringens* were isolated on phylogenetically distinct strains from environmental water sources each obtained from a different poultry farm or processing plant.

Example 2

Characterization of Phages Capable of Infecting *Clostridium perfringens*

The methods from Example 1 were also used in Example 2 where appropriate.

Phage Sterility: Microbial contamination was determined by (1) plating 1 mL aliquots of test sample on LB agar plates and incubating replicate plates at 37° C. and 30° C. for 48 hours and (2) pre-incubating 1 mL aliquots of test sample at 37° C. for 24 hours then plating the samples on LB agar and incubating the plates for 24 hours at 37° C. One set of plates was incubated aerobically and another set anaerobically as indicated. Any bacterial growth at the indicated times denotes contamination.

Phage Purity: Purity of phage stocks was determined by pulsed-field gel electrophoresis (PFGE) of uncut DNA. Approximately 100-200 ng of the phage DNA was electrophoresed in a 1% SeaKem® Gold Agarose (Cambrex, Rockland, Me.) gel with 0.5× Sodium boric acid (1×SB: 10 mM sodium hydroxide pH adjusted to 8.5 with boric acid) buffer at 14° C. in a CHEF Mapper XA PFGE apparatus (Bio-Rad Laboratories, Hercules, Calif.). The run time was 12 hours with a voltage of 6 V/cm and a linearly ramped pulse time of 0.06 seconds to 8.53 seconds. The gels were stained with ethidium bromide and visualized with UV light.

Nucleic Acid Characterization: DNA from each batch of bacteriophage Was isolated by a standard phenol-chloroform extraction method. Proteinase K (200 μg/ml) and RNase A (1 μg/ml) were added to phage samples with a titer≥$1\times10^9$ PFU/ml and incubated at 37° C. for 30 minutes followed by 56° C. for an additional 30 minutes. SDS/EDTA was add to a final concentration of 0.1% and 5 mM respectively and incubated at room temperature for 5 minutes. The samples were extracted once with buffered phenol, once with phenol-chloroform and once with chloroform. Phage DNA was ethanol precipitated and resuspended in 10 mM Tris-HCl (pH 8.0)-0.1 mM EDTA (TE) buffer.

Restriction maps of the phage genomes were made by digesting approximately 1 μg of the phage DNA with 10 units of XmnI (New England Biolabs, Beverly, Mass.) according to the manufacturers' recommendations. Restriction fragments were separated on a 1.0% agarose gel for 16 hours at 20 V in 1× Tris-acetate-EDTA (10×TAE, EMD Chemicals) buffer and bands visualized by staining with ethidium bromide.

Protein Characterization: Phage proteins were analyzed by sodium dodecyl sulfate-polyacrylamide gel electrophoresis (SDS-PAGE). Briefly, phage samples with a titer≥$1\times10^8$ PFU/ml were denatured in a boiling water bath for 5 minutes in NuPAGE® LDS buffer fortified with DTT (Invitrogen, Carlsbad, Calif.). Aliquots were electrophoresed in a precast NuPAGE® Novex 4 to 12% Bis-Tris continuous gradient gel (Invitrogen) at 120 V for 110 minutes. Proteins was visualized on gels by silver-staining using a SilverXPress® (Invitrogen) according to the manufacturers' recommendations.

*Clostridium perfringens* Phage Susceptibility: Forty-six *C. perfringens* strains were screened for their susceptibility to the six monophages and two cocktails by the drop on lawn method. Strains was streaked onto BHI agar plates and incubated at 37° C. anaerobically overnight. One colony of each strain was inoculated into a separate 15-ml culture tube containing BHI broth and incubated at 37° C. anaerobically until the $OD_{600}$ reached 0.1-0.3. One hundred microliters of each strain was mixed with BHI soft-agar and poured onto a BHI agar plate. After the soft-agar hardened 10 μl of each phage was spotted in triplicate onto the plates inoculated with the *C. perfringens* strains. Lytic activity was observed after overnight anaerobic incubation at 37° C.

Preparation of Phage Manufacturing Batches: Shake flask batches of each phage were carried out in 2-L flasks containing 1.5 L of BHI broth. *Clostridium perfringens* strains were grown in BHI broth anaerobically overnight at 37° C., subcultured and grown to an $OD_{600}$ of 0.1-0.3. Cultures were infected at an MOI previously determined to be optimal for each phage (See Table 5.1.4). Growth was monitored spectrophotometrically until lysis occurred and phage harvested by vacuum filtration (Stericup, Millipore). Batches of each phage were concentrated separately and buffer exchanged with PBS by tangential flow filtration in a Pellicon® 2 Mini Cassette using a 50 kDa filter (Millipore).

Endotoxin Levels: Endotoxin levels for all lots of phage produced were determined by a *Limulus* amoebocyte lysate (LAL) assay using a chromogenic assay (QCL-1000 Kit, BioWhittaker, Walkersville, Md.) following the manufacturers' recommendations. A standard curve with *E. coli* endotoxin (supplied with kit) ranging from 0.1 to 1.0 endotoxin units (EU) per milliliter endotoxin was constructed for each assay by plotting the optical density at 405 nm ($OD_{405}$) versus EU/ml. Phage samples were assayed diluted in sterile water (USP, Baxter, Deerfield, Ill.) and the absorbance at 405 nm was measured with a μQuant (Bio-Tek Instruments, Inc., Winooski, Vt.) microplate reader.

Endotoxin concentrations for each sample were calculated by linear regression from the standard curve. Standards and samples were analyzed in triplicate.

Carbohydrate Content: Carbohydrate content for all lots of phage produced was determined by an anthrone method. A standard curve with glucose ranging from 10 to 250 μg/mL was constructed for each assay by plotting the optical density at 625 nm ($OD_{625}$) versus μg/mL of glucose concentration. Phage samples were assayed in PBS and the absorbance at 625 nm was measured with a μQuant™ (Bio-Tek Instruments, Inc.) microplate reader.

Carbohydrate concentrations for each sample were calculated by linear regression from the standard curve. Standards and samples were analyzed in duplicate.

Total Protein Content: The total protein content for all lots of phage produced was determined by a bicinchoninic acid (BCA) assay using a colorimetric assay (BCA™ Protein Assay Kit, Pierce, Rockford, Ill.) following the manufacturer's recommendations. A standard curve with bovine serum albumin (BSA, supplied with kit) ranging from 20 to 2,000 μg/mL protein was constructed for each assay by plotting the optical density at 562 nm ($OD_{562}$) versus μg/mL BSA. The absorbance at 562 nm was measured with a μQuant® (Bio-Tek Instruments, Inc.) microplate reader.

Total protein concentrations for each sample were calculated by linear regression from the standard curve. Standards and samples were analyzed in triplicate.

Electron Microscopy: High-titer phage lysates (≥$10^8$ PFU/ml) were centrifuged 31,000×g for 2 hours and resuspended in 100 mM ammonium acetate (pH 7.0). A drop of phage suspension was deposited on a carbon-coated Formvar copper grid of 400 mesh. The phages were negatively stained by adding a drop of potassium phosphotungstate (1-2%, pH 7) and after one minute the excess fluid was withdrawn. Pictures of the phage particles were taken with a Philips EM 300 transmission electron microscope at an acceleration voltage of 60 kV with a primary magnification of 29,700×.

Results: Six novel bacteriophages that infect *Clostridium perfringens* were isolated from environmental water or sewage sources. Each phage was characterized at both the protein and nucleic acid level. The optimal host strain for propagation of each bacteriophage was identified and all were negative for endogenous phage. (Table 2)

TABLE 2

Optimal *C. perfringens* host strains for propagating *C. perfringens*-specific phages

| Phage | Host |
|---|---|
| CPLV-42 | Cp 27 |
| CPAS-7 | Cp 8 |
| CPAS-12 | Cp 26 |
| CPTA-37 | Cp 27 |
| CPAS-15 | Cp 8 |
| CPAS-16 | Cp 42 |

Stocks of all six monophages and their respective host strains were made for use in characterization and production of each phage.

Figure 4:
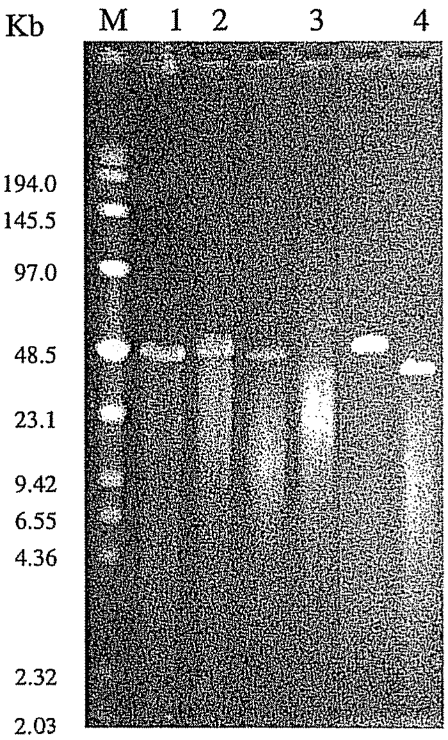
FIG. 4: Pulsed-field gel electrophoresis analysis of undigested phage DNA isolated from each monophage. Lane M, Low Range PFG Marker (NEB); lane 1, CPAS-7; lane 2, CPAS-15; lane 3, CPAS-16; lane 4, CPLV-42; lane 5, CPTA-12; lane 6, CPAS-37.
Figure 5:
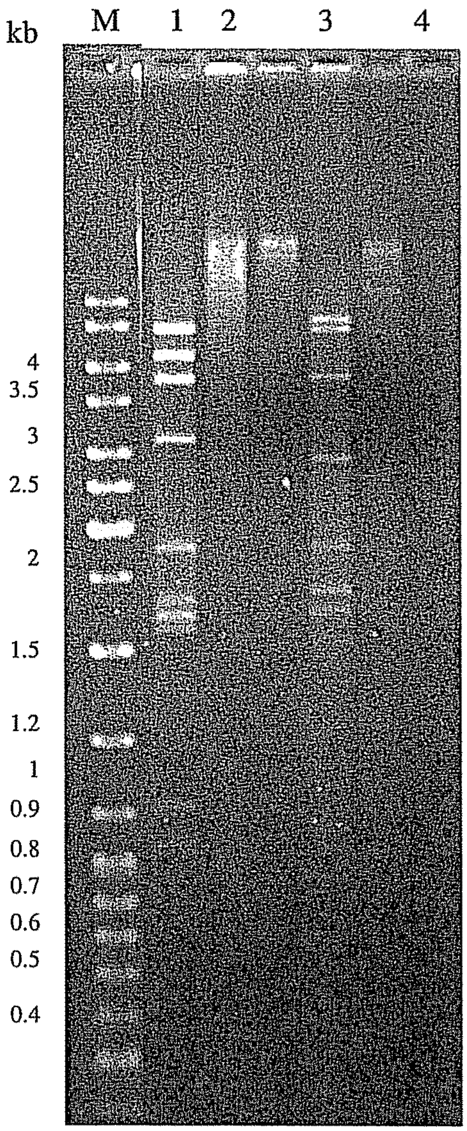
FIG. 5 shows XmnI digested phage DNA from each monophage. Lane M, GeneRuler DNA Ladder Mix (Fermentas); lane 1, CPLV-42; lane 2, CPAS-7; lane 3, CPAS-15; lane 4, CPTA-37; lane 5, CPAS-12; lane 6, CPAS-16.
Figure 6:
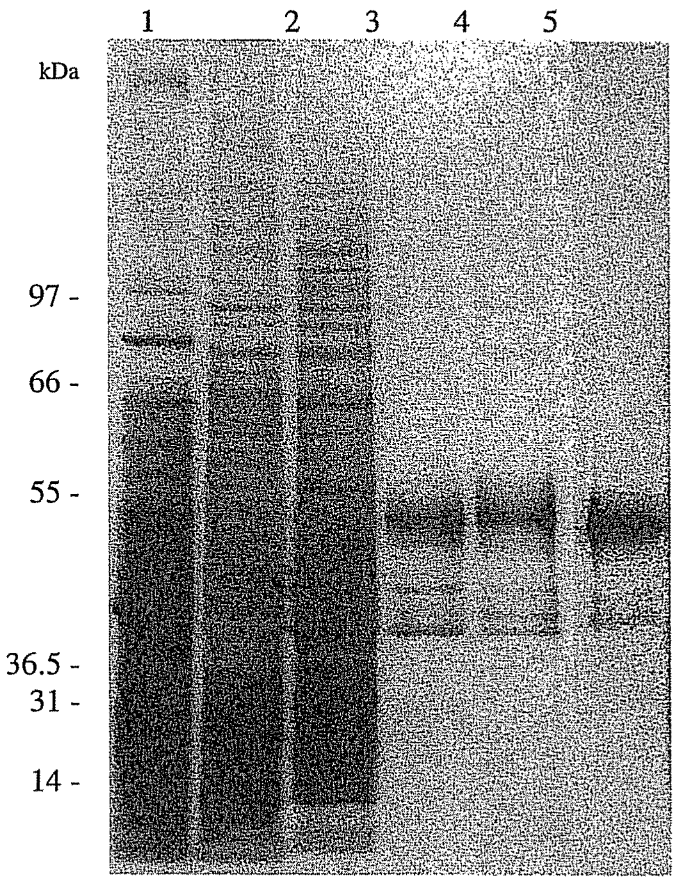
FIG. 6 shows structural protein profiles for each *C. perfringens* monophage. Lane 1, CPLV-42; lane 2, CPAS-12; lane 3, CPAS-7; lanes 4, CPAS-16; lane 5, CPAS-15; lane 6, CPTA-37.

PFGE analysis of uncut DNA from each of the isolated phages showed that they were pure monophages with genome sizes of 36 to 50 kb (FIG. 4). DNA from each of the monophages isolated was digestible with XmnI (FIG. 5). All six of the monophages showed different protein profiles on SDS-PAGE or RFLP profiles confirming that all six monophages are different from one another. (FIG. 6)

Figure 7:
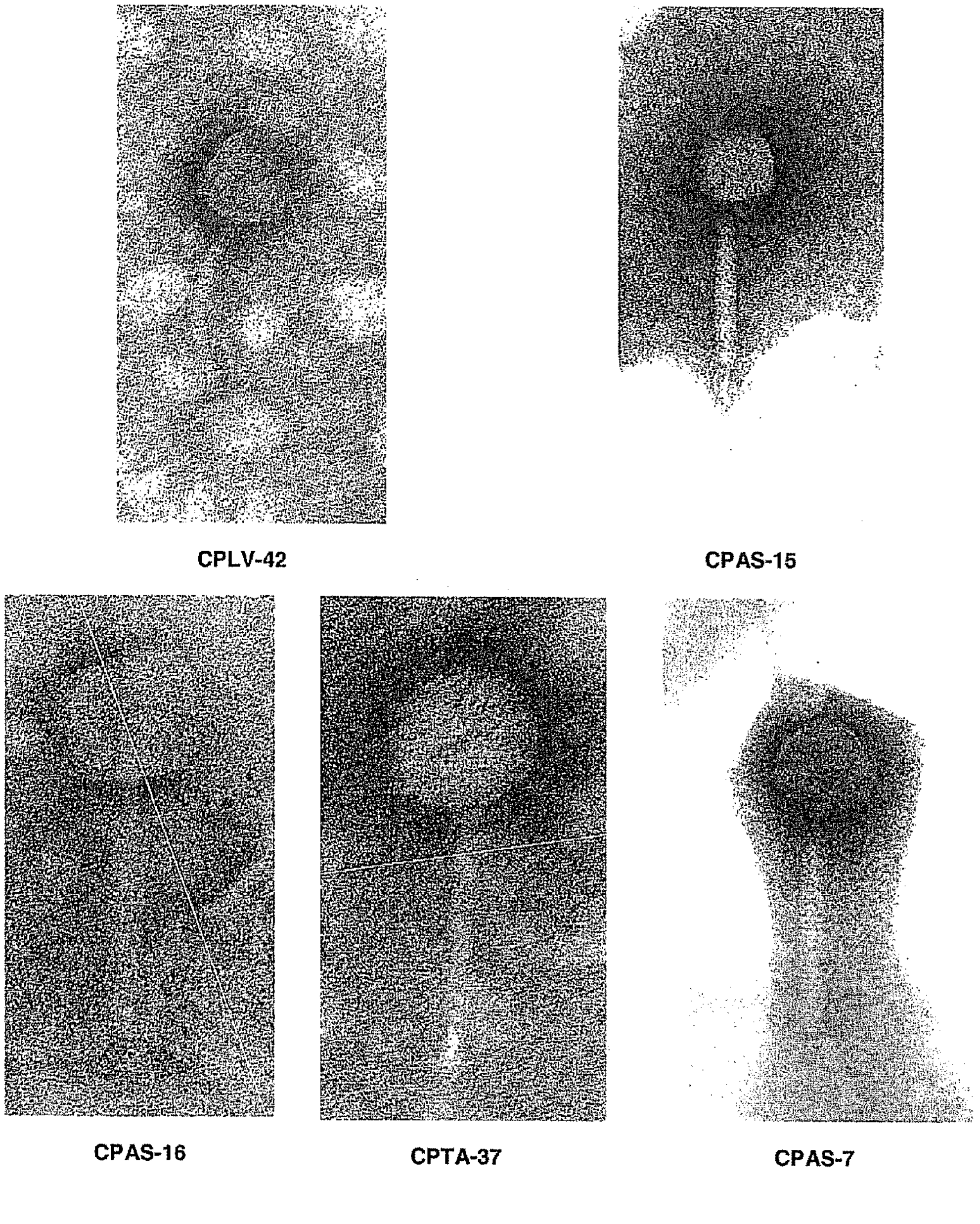
FIG. 7 shows electron micrographs of *C. perfringens* bacteriophages.

Electron microscopy showed the bacteriophages to be members of the Siphoviridae or Myoviridae families of icosahedral head phages (FIG. 7) with long tails and double-stranded DNA genomes.

The ability of the six *C. perfringens*-specific monophages to infect 46 *C. perfringens* strains is shown in Table 3. Phage CPLV-42, CPAS-16, CPTA-37, CPAS-7, CPAS-12, and CPAS-15 infected 20%, 87%, 13%, 39%, 74%, and 52% of the strains screened respectively. The specificity of the phages for *C. perfringens* was examined by screening the susceptibility of ten strains of *E. coli, L. monocytogenes, S. enterica*, and *P. aeruginosa*. None of these 40 strains were infected by any of the monophages isolated against *C. perfringens* (Table 4).

TABLE 3

Susceptibility of *C. perfringens* strains to *C. perfringens*-specific bacteriophages

| Strain | Phage | | | | | | Cocktail | |
|---|---|---|---|---|---|---|---|---|
| | CPLV-42 | CPAS-16 | CPAS-12 | CPAS-15 | CPAS-7 | CPTA-37 | INT-401 | INT-402 |
| ATCC 13124 | + | + | + | + | + | − | + | + |
| Cp 1 | − | + | − | − | − | − | + | + |
| Cp 2 | − | − | + | + | + | − | + | + |
| Cp 3 | − | + | + | − | − | − | + | + |
| Cp 4 | − | + | + | + | − | − | + | + |
| Cp 5 | − | + | + | + | − | − | + | + |
| Cp 6 | − | + | + | − | − | − | + | + |
| Cp 7 | + | + | + | + | + | − | + | + |
| Cp 8 | + | + | − | + | + | − | + | + |
| Cp 9 | − | + | + | + | − | − | + | + |
| Cp 10 | − | + | − | + | − | − | + | + |
| Cp 11 | − | + | + | − | − | − | + | + |
| Cp 12 | − | + | + | − | − | − | + | + |
| Cp 13 | − | + | + | + | − | − | + | + |
| Cp 14 | − | + | − | + | + | − | + | + |
| Cp 15 | + | + | + | − | − | − | + | + |
| Cp 16 | − | + | + | + | + | − | + | + |
| Cp 17 | − | + | + | + | + | − | + | + |
| Cp 19 | − | + | + | − | − | − | + | + |
| Cp 21 | − | + | + | − | − | − | + | + |
| Cp 22 | + | + | + | + | − | − | + | + |
| Cp 23 | − | + | + | + | + | − | + | + |
| Cp 24 | − | + | + | + | − | − | + | + |
| Cp 25 | − | + | + | + | + | − | + | + |
| Cp 26 | − | + | + | − | − | − | + | + |
| Cp 27 | + | + | + | − | − | + | + | + |
| Cp 28 | − | + | − | − | − | − | + | − |
| Cp 29 | − | + | − | − | + | − | + | − |
| Cp 30 | − | + | + | − | − | − | + | + |
| Cp 31 | − | − | + | − | − | − | + | − |
| Cp 32 | + | + | − | + | + | + | + | − |
| Cp 33 | − | + | + | + | − | − | + | − |
| Cp 34 | − | − | − | + | + | + | + | + |
| Cp 35 | − | + | − | + | + | − | + | + |
| Cp 36 | − | − | + | + | − | − | + | + |
| Cp 37 | − | + | + | − | − | − | + | + |
| Cp 38 | − | + | + | + | + | − | + | + |
| Cp 39 | − | + | − | − | − | − | + | + |
| Cp 40 | − | + | − | − | − | − | + | + |
| Cp 41 | − | − | + | − | + | + | + | + |
| Cp 42 | + | + | + | + | + | + | + | + |
| Cp 43 | − | + | + | − | − | − | + | + |
| Cp 44 | − | + | + | − | + | − | + | + |
| Cp 45 | − | + | + | − | − | − | + | + |
| Cp 46 | − | − | − | − | − | − | − | − |
| Cp 47 | + | + | + | + | + | + | + | + |

TABLE 4

Susceptibility of other bacterial strains to *C. perfringens*-specific bacteriophages

| Strain | Phage | | | | | |
|---|---|---|---|---|---|---|
| | CPLV-42 | CPAS-16 | CPAS-12 | CPAS-15 | CPAS-7 | CPTA-37 |
| *Pseudomonas aeruginosa* | | | | | | |
| Pa 1 | − | − | − | − | − | − |
| Pa 3 | − | − | − | − | − | − |
| Pa 7 | − | − | − | − | − | − |
| Pa 15 | − | − | − | − | − | − |
| Pa 21 | − | − | − | − | − | − |
| Pa 33 | − | − | − | − | − | − |
| Pa 42 | − | − | − | − | − | − |
| Pa 62 | − | − | − | − | − | − |
| Pa 65 | − | − | − | − | − | − |
| Pa 72 | − | − | − | − | − | − |

TABLE 4-continued

Susceptibility of other bacterial strains to *C. perfringens*-specific bacteriophages

| Strain | Phage CPLV-42 | CPAS-16 | CPAS-12 | CPAS-15 | CPAS-7 | CPTA-37 |
|---|---|---|---|---|---|---|
| *Salmonella enterica* | | | | | | |
| SE 24 | – | – | – | – | – | – |
| SS 28 | – | – | – | – | – | – |
| ST 31 | – | – | – | – | – | – |
| SHE 43 | – | – | – | – | – | – |
| SH 49 | – | – | – | – | – | – |
| S 45 | – | – | – | – | – | – |
| S AE 72 | – | – | – | – | – | – |
| SK 103 | – | – | – | – | – | – |
| SR 114 | – | – | – | – | – | – |
| SH 162 | – | – | – | – | – | – |
| *Listeria monocytogenes* | | | | | | |
| Lm 6 | – | – | – | – | – | – |
| Lm 10 | – | – | – | – | – | – |
| Lm 23 | – | – | – | – | – | – |
| Lm 31 | – | – | – | – | – | – |
| Lm 35 | – | – | – | – | – | – |
| Lm 49 | – | – | – | – | – | – |
| Lm 62 | – | – | – | – | – | – |
| Lm 67 | – | – | – | – | – | – |
| Lm 79 | – | – | – | – | – | – |
| Lm 86 | – | – | – | – | – | – |
| *Escherichia coli* | | | | | | |
| Ec 3 | – | – | – | – | – | – |
| Ec 26 | – | – | – | – | – | – |
| Ec 37 | – | – | – | – | – | – |
| Ec 41 | – | – | – | – | – | – |
| Ec 56 | – | – | – | – | – | – |
| Ec 60 | – | – | – | – | – | – |
| Ec 65 | – | – | – | – | – | – |
| Ec 68 | – | – | – | – | – | – |
| Ec 73 | – | – | – | – | – | – |
| Ec 77 | – | – | – | – | – | – |

The following strains were used to demonstrate the overall activity of the phage cocktail TNT-401, versus a standardized set of *Clostridium perfringens* strains available from depositories. Strains were evaluated for lysis by spotting 10 microliters containing $10^8$ pfu/ml onto pure lawns of each test strain spread onto BHI agar, and incubating overnight at 37° C.

TABLE 5

| Depository | Strain Identifier Number | INT-401 Lysis |
|---|---|---|
| ATCC | 25768 | + |
| ATCC | 3624 | + |
| ATCC | 9856 | + |
| ATCC | 3628 | + |
| ATCC | 13124 | + |
| ATCC | PTA-8495 | + |
| NRRL | B-50143 (CP8) | + |
| NRRL | B-50144 (CP26) | + |
| NRRL | B-50145 (CP42) | + |

6 monophages were then isolated. (Table 6) Two phage cocktails, INT-401 (CPAS-7, CPAS-12, CPAS-15, CPAS-16, and CPLV-42) and INT-402 (CPAS-12, CPAS-15, CPAS-16, CPLV-42), were prepared from five of the six monophages isolated. Table 7 gives the levels of endotoxin, total carbohydrate, and total protein in *C. perfringens*-specific cocktails. Both cocktails were effective in killing greater than 85% of the 46 *C. perfringens* strains screened. INT-401 was selected for use in proof-of-principle efficacy studies designed to determine the prevention of necrotic enteritis in *C. perfringens* challenged broiler chickens. This cocktail contains the five bacteriophages with the broadest host range and is likely to provide a broader (compared to INT-402) spectrum of activity in actual use against wild-type *C. perfringens* strains.

TABLE 6

Summary of *C. perfringens* monophage batch preparation

| Phage | Host Strain | MOI | Culture Time (h) | Titer (PFU/ml) |
|---|---|---|---|---|
| CPLV-42 | Cp 27 | 1 | 5 | $5 \times 10^{10}$ |
| CPAS-16 | Cp 42 | 1 | 3 | $1 \times 10^8$ |
| CPAS-12 | Cp 26 | 1 | 4-5 | $1 \times 10^8$ |
| CPTA-37 | Cp 27 | 1 | 4.5 | $4 \times 10^8$ |
| CPAS-7 | Cp 8 | 1 | 4-5 | $5 \times 10^8$ |
| CPAS-15 | Cp 8 | 1 | 4-5 | $6 \times 10^9$ |

TABLE 7

| Levels of endotoxin, total carbohydrate, and total protein in *C. perfringens*-specific cocktails | | |
|---|---|---|
| Content | INT-401 | INT-402 |
| Endotoxin (EU/ml) | 384 | 288 |
| Total Carbohydrate (μg/ml) | 170 | 43 |
| Total protein (μg/ml) | 661 | 175 |

Example 3

Protocol for Bacteriophage Treatment as Therapy or Prevention of Necrotic Enteritis in Broiler Chickens Challenged with *Clostridium Perfringens*

Broiler chickens: A total of 576 male day-old broiler chickens were assigned to treatment on day 0. There were no vaccinations (Mareks or Bronchitis) or antibiotics applied to eggs or chicks at the hatchery.

Housing: The 64-pen broiler chicken research facility at Maple Leaf Agresearch was used to conduct the study. Forty-eight pens, each providing approximately 10 square feet of floor space, were assigned to treatment groups. Each pen had a concrete floor and nylon mesh partitions supported by PVC frame. Adjacent pens were separated by a solid 12-inch high plastic barrier at bird level. Each pen was permanently identified by number and contained 12 birds on day zero. The barn was heated by two natural gas heaters, which were equally spaced and positioned to warm incoming air at the south wall of the building. Air was exhausted by fans located on the north-facing wall of the building. Each pen contained one nipple-type drinker, which provided clean drinking water ad libitum. Water was de-chlorinated. Dry feed was provided ad libitum in trough-type feeders (one per pen) of 5-kg capacity. New wood shavings were used as bedding.

Management: Lighting program, barn temperature, litter type and other management practices were typical of commercial broiler chicken producers in the local geographic area and is fully documented in the raw data. Birds, which were moribund and unable to reach food or water, were culled and euthanized by carbon dioxide gas.

Bodyweight, pen number, date of death and cause of death were determined by necropsy and recorded for each bird culled or found dead during the study.

Experimental design: A randomized complete block design was used to study the effects of eight treatments. The treatments were as follows:

TABLE 8

| Treatment design | | |
|---|---|---|
| Treatment code | *C. perfringens* Challenge | Test Article |
| 1 | No | No |
| 2 | Yes | No |
| 3 | Yes | Yes |
| 4 | Yes | Yes |
| 5 | Yes | Yes |
| 6 | Yes | Yes |
| 7 | Yes | Yes |
| 8 | Yes | Yes |

There were 8 pens per block (8 treatments) and 6 blocks (replicates) for a total of 48 pens. (See Section 4.2, Deviation #2 for change to above treatment to block assignment).

Treatment Groups:

Treatment 1—Control-UUC (no *C. perfringens* challenge or bacteriophage administration)

Treatment 2—Control-IUC (*C. perfringens* challenge without bacteriophage cocktail)

Treatment 3—In ovo injection of phage cocktail at day 18 of incubation.

Treatment 4—Spray application of phage cocktail to chicks after hatching.

Treatment 5—In ovo injection of phage cocktail at day 18 of incubation and spray application of phage cocktail to chicks after hatching.

Treatment 6—In ovo injection of phage cocktail at day 18 of incubation, spray application of phage cocktail to chicks after hatching and oral gavage of bacteriophage cocktail on Day 7 through 13.

Treatment 7—Bacteriophage cocktail administered via oral gavage from Day 7 through Day 13 (oral gavage ceased on day of *Clostridium perfringens* challenge)

Treatment 8—Bacteriophage cocktail administered via oral gavage beginning on Day 14 (concurrent with *Clostridium perfringens* challenge) through Day 18.

Feeding program: The following feeding program was used in the study:

TABLE 9

| Feeding program | | |
|---|---|---|
| Day | Feed Type | Formulation number* |
| 0-13 | Starter | 282 |
| 9:00 p.m. Day13 to 9:00 a.m. Day 14 | None. Feed was withdrawn | None |
| 14-21 | Starter | 282 |

Feed sampling: The investigator's representative was present during feed manufacture. Ten representative samples were taken from each batch of final feed, composited and divided into three samples for proximate analysis, and retainer samples, respectively.

Administration of *Clostridium perfringens* challenge: A *Clostridium perfringens* isolate originating from a field case of necrotic enteritis in Ontario was used in the study. Inoculum contained approximately $10^8$ cfu *Clostridium perfringens* per mL at time of feeding. Feed was withdrawn from all birds for approximately 8 hours prior to first introduction of challenge. Inoculum was administered to birds via feed in the afternoon and night commencing Day 14 P.M. and ending Day 15 A.M. using trough-type feeders. A suitable quantity of assigned feed (approximately 0.150 kg) and an amount of inoculum equal to approximately 1.5 times the weight of feed was added to each feeder. When this procedure was complete for all pens assigned to challenge, feeders were returned to their corresponding pens. Inoculum-feed mixture remaining at the end of the half-day period was weighed and discarded.

Lesion scoring of sacrificed birds: Three birds were randomly selected from each pen on Day 16 and euthanized. These birds were scored grossly for necrotic enteritis and coccidiosis lesions:

TABLE 10

| Necrotic enteritis scoring | |
|---|---|
| Necrotic enteritis score | Description |
| 0 | Normal, no evidence of gross lesions |
| 1 | Thin, friable small intestine |
| 2 | Focal necrosis and/or ulceration |
| 3 | Patchy necrosis |
| 4 | Severe extensive necrosis (typically seen in birds which have died from NE) |

*Clostridium perfringens* culture of small intestinal segment: A small intestinal segment was collected from 40 birds that died on or after Day 15 and had a gross diagnosis of necrotic enteritis. The segment was forwarded to the Department of Pathology at the University of Guelph for *C. perfringens* culture. Culture results were reported as positive or negative for *C. perfringens*. Samples of positive bacterial cultures were forwarded to Intralytix for testing for phage susceptibility. In addition, 144 ileum samples were collected from the birds sacrificed for *C. perfringens* lesion scoring on Day 16. These samples were quantitatively tested for *C. perfringens* at the above referenced laboratory and microbiological samples were forwarded to Intralytix for additional characterization of phage activity.

Necropsy: All birds that died or were euthanized were submitted to the study pathologist for gross necropsy to determine the cause of death.

Observations and Calculation of Variables:

1) Bodyweight and number of birds per pen on Days 0, 14, and 21.
2) Amounts of each feed consumed by each pen.
3) Bodyweight and date of death for birds which were culled or died.
4) Feed conversion ratio was calculated on a pen basis as feed consumed/[total weight of live birds+total weight of dead and culled birds+total weight of sacrificed birds] for the 0-14, 14-21 and 0-21 Day periods.
5) Average bodyweight per pen was calculated as total weight of live birds at time of weighing/number of live birds at time of weighing.
6) Daily feed intake (grams) per live bird day was calculated on a pen basis for Day 0-14, Day 14-21 and Day 0-21.
7) Apparent cause of death was recorded for all birds that died or were culled. Total mortality and mortality from necrotic enteritis will be calculated on a pen basis.
8) Evaluation of the effects of the in ovo injection treatments on percent hatch and chick health at the hatchery.
9) Necrotic enteritis lesion score of sacrificed birds (Day 16)
10) Birds were observed on a flock basis at least once daily and observations recorded.

Test substance disposition: Remaining bacteriophage cocktail test substance was destroyed by incineration and destruction is documented in the study records.

Bird disposition: Birds (treated and control) were humanely euthanized at the end of the study and disposed of via incineration and method and date of disposition was recorded in the study records. Hatchery waste and unused in ovo bacteriophage injected eggs were disposed of via incineration. Hatched chicks that had been in ovo injected or sprayed with bacteriophage but not assigned to the study, were humanely euthanized and disposed of via incineration.

Original data: Original data is submitted to the sponsor together with the final report. An exact copy of the final report and data will be maintained at Maple Leaf Agresearch for a minimum of two years.

Documentation: All raw (original) data was recorded in black ink on data sheets bearing the trial number. Corrections were made by drawing a single line through the original entry and writing the correct entry beside it together with initials of the person making the correction, the date the correction was made and the reason for the correction. Defined error codes were used to record reason for correcting a data point.

Statistical analysis: Randomized complete block design was be used. Pen location within the facility was the blocking factor. The pen was the experimental unit for statistical analysis. A one-way treatment structure was utilized with each treatment being replicated six times (once within each block, except as detailed in Deviation #2, Section 4.2). Mortality data was transformed using an arcsine transformation prior to analysis of variance. Mixed models analysis was used to analyze all data. Means were compared using an appropriate multiple range test.

Amendment #1: This amendment clarified dates, eliminated vaccine administration and any potential interference vaccine might have with the Test Article, and detailed exact doses of Test article to be administered during "in ovo" injection (0.2 mL), spraying (about 7 mL per 100 chicks) and oral dosing (0.5 mL per bird per day).

Amendment #2: This amendment redefined the dosages of "in ovo" administration (0.05 mL per egg) and spray (7 to 22 mL per 100 chicks). The upper range of 22 mL was actually used for the spray.

Deviations: Two deviations occurred and are described in the Protocol section of the Study Binder. A brief description follows:

Deviation #1: Only 12 birds were assigned to pens instead of the 15 described in the protocol. This will have an impact on the statistical power of the study, particularly the mortality data.

Deviation #2: Block 3 was assigned two treatment 2 pens and no treatment 5 pen causing an imbalance in the design. Least square means will be reported to correct for the unequal representation per treatment group. This is not expected to have a major influence on the power of the study.

Example 4

Results for Bacteriophage Treatment as Therapy or Prevention of Necrotic Enteritis in Broiler Chickens Challenged with *Clostridium Perfringens*

The results of this study are summarized in Tables 10 to 12. A detailed statistical analysis was performed.

Hatchery: "In ovo" injection of eggs with Test Article (0.05 mL per egg) for Treatments 3, 5 and 6 was performed at 18 days of incubation using an Embrex machine and followed the standard industry protocol with the following exceptions: Marek's vaccine and antibiotic (Excenel) were not included. This standard procedure also involved applying a small amount of chlorine solution over the injection hole just post injection. For this trial, 1259 fertile eggs were transferred without being injected and hatched at 96.6%. The 775 fertile eggs injected with Test Article hatched at 95.5%.

TABLE 11

Delivery Routes of Bacteriophage on weights of broiler chickens challenged with necrotic enteritis

| | Average live weights (kg) | | | | |
|---|---|---|---|---|---|
| Treatment[1] | Day 0 | Day 14 | Day 21 | Day 35 | Day 42 |
| Control | .046 | .330 | .750$^{A}$ | 1.917$^{A}$ | 2.776$^{A}$ |
| Challenged control | .046 | .340 | .618$^{C}$ | 1.530$^{C}$ | 2.342$^{C}$ |
| BMD control | .045 | .340 | .634$^{C}$ | 1.795$^{B}$ | 2.686$^{AB}$ |
| Gavaged phage | .045 | .328 | .641$^{C}$ | 1.762$^{B}$ | 2.601$^{B}$ |
| Phage in water | .046 | .348 | .694$^{B}$ | 1.812$^{AB}$ | 2.664$^{AB}$ |
| Phage in feed | .045 | .333 | .658$^{BC}$ | 1.754$^{B}$ | 2.592$^{B}$ |
| SEM[2] | .000 | .010 | .018 | .045 | .059 |
| Pr > F | .5309 | .7492 | .0003 | .0001 | .0004 |

[1]LSMEANS were provided for each treatment. The treatment groups included a control, challenged control, BMD 50 g/ton as a medicated control, oral gavaged phage, phage provide via water and phage provide via feed. The bacteriophage used was Intralytix *C. perfringens* Phage Cocktail - 4.8 x $10^9$ pfu/ml. On Day 14, all birds were orally inoculated with a coccidial inoculum containing approximately 5,000 oocysts of *E. maxima* per bird. All groups, except the control, were challenged with *Clostridium perfringens* on Days 18, 19, and 20. Oral Administration of phage cocktail via gavages, drinking water and feed application will occurred on days 17, 18, 19, 20, and 21.

[2]Standard error of the LSMEANS.

$^{A,B,C}$Means within columns with different superscripts are significantly different (P < .05).

Three Treatments (#'s 4, 5 and 6, Table 10) were also sprayed with Test Article at the hatchery after hatch. A commercial spray cabinet designed for administering coccidiosis vaccine was used to deliver the Test Article at a rate of 22 mL per box or approximately 0.22 mL per bird. These birds were held in the hatchery for an extra ½ hour to permit drying prior to transport to the research farm.

Challenged pens were provided with 1.66 kg of the *Clostridia perfringens* inoculum/feed mixture and all consumed at least 1.25 kg except one, a challenged control pen. This pen suffered from severe water restriction due to a technical problem and for this reason was removed from the analysis. Due to the deviation described above the challenged control (Treatment 2) was assigned one extra pen and Treatment 5 one less pen. With this slight imbalance in design, least square means are reported. There was no significant (P>0.05) difference between challenged groups in quantity of inoculum consumed.

The primary criteria for evaluating the effectiveness of Test Article and its method of administration is mortality attributable directly to *Clostridia perfringens* challenge. No birds died from Necrotic Enteritis (NE) in the non-challenged control (Treatment 1) and this was significantly (P<0.01) different than the challenged control with 25.9% percent of birds in a pen dying of NE. Birds treated (Treatment 8) by Oral Gavage (OG) from the day of challenge (day 14) until day 18 had the lowest mortality (5.6%) of the phage treated groups and this was not significantly (P>0.05) different from the non-challenged control (Treatment 1). Two of the "In ovo" groups (Treatments 3 and 6) had intermediate NE mortality, which was not significantly (P>0.05) different from either Control groups (Treatments 1 and 2).

Three birds per pen were sacrificed at Day 16 to detect lesions typical of NE and to determine the presence of *Clostridia perfringens* in either a defined segment (approximately 3 to 4 cm distal to the duodenum) if no lesions were present or a segment surrounding an identified lesion. Although not significantly (P>0.05) different from the other treatment groups, there were no "typical" NE lesions found in the non-challenged control (Treatment 1). No significant (P>0.05) difference between treatments was found for lesion scores.

*Clostridia perfringens* (Cp) bacterium were isolated from all groups including the non-challenged control. We do not know if the strain isolated from the non-challenged control was the same as the challenged strain. However, Treatment 1 was numerically lower for Bacterial Scores for Cultures and this was consistent with the significantly (P<0.05) lowest score (Table 1) for Smears. No other trends were evident in the Bacterial Score means for either Cultures or Smears between the other treatment groups.

TABLE 12

Delivery Routes of Bacteriophage on weight gains of broiler chickens challenged with necrotic enteritis

| | Average weight gain(kg) | | | | |
|---|---|---|---|---|---|
| Treatment[1] | Days 0-14 | Days 0-21 | Days 14-21 | Days 0-35 | Days 0-42 |
| Control | .284 | .705$^{A}$ | .421$^{A}$ | 1.871$^{A}$ | 2.730$^{A}$ |
| Challenged control | .294 | .572$^{C}$ | .278$^{C}$ | 1.484$^{C}$ | 2.296$^{C}$ |
| BMD control | .295 | .589$^{C}$ | .294$^{C}$ | 1.750$^{B}$ | 2.641$^{AB}$ |
| Gavaged phage | .283 | .596$^{C}$ | .313$^{BC}$ | 1.716$^{B}$ | 2.556$^{B}$ |
| Phage in water | .302 | .648$^{B}$ | .346$^{B}$ | 1.766$^{AB}$ | 2.618$^{AB}$ |
| Phage in feed | .287 | .612$^{BC}$ | .325$^{BC}$ | 1.709$^{B}$ | 2.547$^{B}$ |
| SEM[2] | .010 | .018 | .014 | .045 | .059 |
| Pr > F | .7559 | .0003 | .0001 | .0001 | .0004 |

[1]LSMEANS were provided for each treatment. The treatment groups included a control, challenged control, BMD 50 g/ton as a medicated control, oral gavaged phage, phage provide via water and phage provide via feed. The bacteriophage used was Intralytix *C. perfringens* Phage Cocktail - 4.8 x $10^9$ pfu/ml. On Day 14, all birds were orally inoculated with a coccidial inoculum containing approximately 5,000 oocysts of *E. maxima* per bird. All groups, except the control, were challenged with *Clostridium perfringens* on Days 18, 19, and 20. Oral Administration of phage cocktail via gavages, drinking water and feed application will occurred on days 17, 18, 19, 20, and 21.

[2]Standard error of the LSMEANS.

$^{A,B,C}$Means within columns with different superscripts are significantly different (P < 0.05).

There was a significantly (P<0.05) higher chick weight for one of the groups (Treatment 4) receiving Test Article by Spray at the hatchery. This was not significantly different than one (Treatment 5) of the other two groups receiving the Spray. This may be a result of these Treatments retaining more moisture from the Spray procedure. Pre-challenge, on Day 14, there were no significant differences (P>0.05) in body weight between the Treatments. After challenge, at Day 21, the non-challenged control (Treatment 1) was significantly (P<0.05) heavier than the birds receiving Test Article by Oral Gavage (Treatment 7) prior to challenge. No other differences in growth performance were detected.

Total mortality in the non-challenged control was high at 13.9%. As indicated in the necropsy records much of this non-NE mortality was due to internal infections, omphalitis (yolk sac infections) and sudden death. This high early chick mortality is not typical. Total mortality was significantly (P<0.05) lower for the non-challenged control (Treatment 1, 13.9%) and the birds receiving Oral Gavage from day 14 to day 18 (Treatment 8, 12.5%) than Treatment 5 (37.0%).

TABLE 13

Delivery Routes of Bacteriophage on feed conversion of broiler chickens challenged with necrotic enteritis

| | Feed conversion ratio (feed to gain)[2] | | | | |
|---|---|---|---|---|---|
| Treatment[1] | Days 0-14 | Days 0-21 | Days 14-21 | Days 0-35 | Days 0-42 |
| Control | 1.703 | 1.532$^{D}$ | 1.417$^{C}$ | 1.709$^{D}$ | 1.892$^{D}$ |
| Challenged control | 1.600 | 1.912$^{A}$ | 2.284$^{A}$ | 2.483$^{A}$ | 3.226$^{A}$ |
| BMD control | 1.561 | 1.829$^{AB}$ | 2.130$^{A}$ | 2.077$^{B}$ | 2.652$^{B}$ |
| Gavaged phage | 1.662 | 1.760$^{BC}$ | 1.864$^{B}$ | 1.814$^{CD}$ | 2.086$^{C}$ |
| Phage in water | 1.562 | 1.676$^{C}$ | 1.778$^{B}$ | 1.813$^{CD}$ | 2.066$^{C}$ |

TABLE 13-continued

Delivery Routes of Bacteriophage on feed conversion of broiler chickens challenged with necrotic enteritis

| | Feed conversion ratio (feed to gain)[2] | | | | |
|---|---|---|---|---|---|
| Treatment[1] | Days 0-14 | Days 0-21 | Days 14-21 | Days 0-35 | Days 0-42 |
| Phage in feed | 1.680 | $1.777^{ABC}$ | $1.868^{B}$ | $1.841^{C}$ | $2.089^{C}$ |
| SEM[3] | .045 | .051 | .081 | .047 | .039 |
| Pr > F | .1359 | .0002 | .0001 | .0001 | .0001 |

[1]LSMEANS were provided for each treatment. The treatment groups included a control, challenged control, BMD 50 g/ton as a medicated control, oral gavaged phage, phage provide via water and phage provide via feed. The bacteriophage used was Intralytix *C. perfringens* Phage Cocktail - 4.8 x $10^9$ pfu/ml. On Day 14, all birds were orally inoculated with a coccidial inoculum containing approximately 5,000 oocysts of *E. maxima* per bird. All groups, except the control, were challe Oral Administration of phage cocktail via gavages, drinking water and feed application will occurred on days 17, 18, 19, 20, and 21.
[2]The feed conversion ratio was adjusted for the weights of mortality and removed weights.
[3]Standard error of the LSMEANS.
[A,B,C,D]Means within columns with different superscripts are significantly different (P < 0.05).

TABLE 14

Delivery Routes of Bacteriophage on mortality and lesion scores of broiler chickens challenged with necrotic enteritis

| | Mortality (%)[2] | | | | Necrotic |
|---|---|---|---|---|---|
| | Totals include all causes | | | Necrotic | enteritis |
| Treatment[1] | Days 0-21 | Days 0-35 | Days 0-42 | enteritis Days 0-42 | lesion scores[3] |
| Control | $2.67^{CD}$ | $2.67^{D}$ | $4.00^{D}$ | $0^{D}$ | $0^{B}$ |
| Challenged control | $41.33^{A}$ | $66.00^{A}$ | $66.67^{A}$ | $64.00^{A}$ | $.9^{A}$ |
| BMD control | $24.67^{B}$ | $51.33^{B}$ | $53.33^{B}$ | $50.00^{B}$ | $1.1^{A}$ |
| Gavaged phage | $10.00^{C}$ | $16.67^{C}$ | $18.00^{C}$ | $14.00^{C}$ | $.1^{B}$ |
| Phage in water | $.67^{D}$ | $67^{D}$ | $3.33^{D}$ | $0^{D}$ | $.1^{B}$ |
| Phage in feed | $2.00^{CD}$ | $3.33^{D}$ | $5.33^{D}$ | $.66^{D}$ | $.4^{B}$ |
| SEM[4] | 2.97 | 2.71 | 2.81 | 2.76 | .2 |
| Pr > F | .0001 | .0001 | .0001 | .0001 | .0006 |

[1]LSMEANS were provided for each treatment. The treatment groups included a control, challenged control, BMD 50 g/ton as a medicated control, oral gavaged phage, phage provide via water and phage provide via feed. The bacteriophage used was Intralytix *C. perfringens* Phage Cocktail - 4.8 x $10^9$ pfu/ml. On Day 14, all birds were orally inoculated with a coccidial inoculum containing approximately 5,000 oocysts of *E. maxima* per bird. All groups, except the control, were challenged with *Clostridium perfringens* on Days 18, 19, and 20. Oral Administration of phage cocktail via gavages, drinking water and feed application will occurred on days 17, 18, 19, 20, and 21.
[2]Percentage data were analyzed with and without transformation (arc sin square root).
[3]On Day 22, scoring was based on a 0 to 3 score, with 0 being normal and 3 being the most severe.
[4]Standard error of the LSMEANS.
[A,B,C,D]Means within columns with different superscripts are significantly different (P < .05).

The non-challenged control (Treatment 1) had the numerically highest (102 grams per bird per day) feed intake and this was significantly (P<0.05) more than Treatment 5 (84 grams per bird per day). Although the means comparison was not significant (P>0.05), Treatment 8 had the numerically best FCR (1.477) of the Phage treated groups and equal to the performance of the non-challenged control.

Conclusions

1. A successful *Clostridia perfringens* (Cp) challenge was achieved. The positive control had 25.9% of the birds die of Necrotic Enteritis compared to the negative control (0.0%).
2. Oral Gavage of Test Article to birds on the day of challenge (Day 14) and for the next four days significantly reduced mortality due to NE. Growth performance in this group was numerically equivalent to the Non-Challenged control.
3. Two of the three "In ovo" treatments had numerically reduced NE mortality (9.6 and 14.8%) when compared to the Challenged control (25.9%).
4. Oral Gavage of Test Article prior to challenge was ineffective in preventing NE mortality due to Cp challenge.
5. Spray of Test Article to chicks at the hatchery did not significantly (P>0.05) reduce NE mortality from Cp challenge.
6. The precision of this trial was reduced by several factors including fewer birds being assigned to pens at day old than specified in the protocol and high early non-challenge related mortality.

Example 5

Sequence Analysis of *C. perfringens* Bacteriophage

Media: Brain Heart Infusion (BHI) broth or BHI agar supplemented with 250 mg/L cycloserine was used to grow all *C. perfringens* isolates. Luria-Bertani (LB) broth and LB agar was used to grow all aerobic strains. All media were obtained from EMD Chemicals, Gibbstown, N.J.

Microorganisms: *Clostridium perfringens* strains were from the Intralytix, Inc. Culture Collection, Baltimore, Md. As part of the collection process, isolates were checked for purity and frozen at −80° C. in 30% glycerol. Most of the work was performed in an anaerobic chamber (Plas-labs, Lansing, Mich.), that contained a 90% $N_2$-5% $H_2$-5% $CO_2$ atmosphere. *Escherichia coli, Listeria monocytogenes, Salmonella enterica*, and *Pseudomonas aeruginosa* strains were from the Intralytix, Inc. Culture Collection and all were grown aerobically.

Bacteriophage: All bacteriophages were isolated from environmental water, industrial wastewater, or sewage sources.

Phage DNA Isolation: DNA from each batch of bacteriophage was isolated by a standard phenol-chloroform extraction method. Proteinase K (200 µg/mL) and RNase A (1 µg/mL) were added to phage samples with a titer≥$1\times10^9$ PFU/ml and incubated at 37° C. for 30 minutes followed by 56° C. for an additional 30 minutes. SDS/EDTA was add to a final concentration of 0.1% and 5 mM respectively and incubated at room temperature for 5 minutes. The samples were extracted once with buffered phenol, once with phenol-chloroform and once with chloroform. Phage DNA was ethanol precipitated and resuspended in 10 mM Tris-HCl (pH 8.0)-0.1 mM EDTA ('1'E) buffer.

Phage Sequencing: The DNA from each of the phages was sequenced using standard automated sequencing methods.

Sequence Analysis: To identify the predicted open reading frames (ORFs) WPA uses a combination of CRITICA (1) and GLIMMER (2). The results from these programs are combined and the optimal open reading frames are extracted from the combined data set.

Each of the two programs uses different algorithms for identifying open reading frames, and each has its benefits and drawbacks. However, by combining the output from both tools WPA is able to optimize the predicted ORFs that they can identify.

WPA uses an automated annotation system in which assignments are generated primarily by sequence similarity searches between the de novo identified ORFs and other ORFs in their databases. In this case, the BLAST algorithm was used to compare predicted protein sequences for the annotation. In addition to the publicly available databases for comparison WPA has a phage database that contains approximately 400 phage genomes which they feel represents the best phage dataset available.

Following the automated annotation and assignment phase, the assignments for each gene are manually curated by Intralytix to see if any of the 17 undesirable genes (Table 15) are present.

TABLE 15

List of undesirable genes encoded in bacteriophage genomes

| Toxin and its Encoding Gene | Bacterial Pathogen |
|---|---|
| Enterotoxin A (entA) | *Staphylococcus aureus* |
| Enterotoxin A (sea, sel) | *Staphylococcus* |
| Enterotoxin A (sea) | *Staphylococcus aureus* |
| Staphylokinase (sak) | *Staphylococcus aureus* |
| Enterotoxin P (sep) | *Staphylococcus aureus* |
| Exfoliative toxin A (eta) | *Staphylococcus aureus* |
| Diphtheria toxin (tox) | *Corynebacterium diphtheriae* |
| Shiga toxins (stx1, 2) | *Escherichia coli* |
| Cytotoxin (ctx) | *Pseudomonas aeruginosa* |
| Cholera toxin (ctxA) | *Vibrio cholerae* |
| Cholera toxin (ctxB) | *Vibrio cholerae* |
| Zonula occludens toxin (zot) | *Vibrio cholerae* |
| Neurotoxin (C1) | *Clostridium botulinum* |
| Enterohaemolysin (hly) | *Escherichia coli* |
| Streptococcal exotoxin A (speA) | *Streptococcus pyogenes* |
| Streptococcal exotoxin C (speC) | *Streptococcus pyogenes* |
| Streptococcal exotoxin K (speK) | *Streptococcus pyogenes* |

Five of the six phages were sequenced. The sequences of each of the five phage genomes were obtained and each predicted open reading frame identified in each genome (Table 16). Each of the predicted genes was annotated. None of the 17 undesirable genes (Table 15) were found in the genomes of any of the five phages for which sequences were available (Table 17).

TABLE 16

Number of predicted ORFs for each *C. perfringens*-specific bacteriophage

| Phage | Number of Open Reading Frames (ORFs) |
|---|---|
| 1 | 67 |
| 2 | 77 |
| 3 | 69 |
| 4 | 47 |
| 5 | 67 |

TABLE 17

Annotations of all predicted genes for each *C. perfringens*-specific bacteriophage genome

| Gene ID | Annotated Function |
|---|---|
| CPAS-7 | |
| 1 | Presumed portal vertex protein |
| 2 | Ring-infected erythrocyte surface antigen |
| 3 | Hypothetical protein |
| 4 | Hypothetical protein |
| 5 | FKBP-type peptidyl-prolyl cis-trans isomerase (trigger factor) |
| 6 | Isocitrate dehydrogenase kinase/phosphatase |
| 7 | Phage-like element PBSX protein xkdH |
| 8 | Phase 1 flagellin |
| 9 | Type I restriction-modification system restriction subunit (EC 3.1.21.3) |

TABLE 17-continued

Annotations of all predicted genes for each *C. perfringens*-specific bacteriophage genome

| Gene ID | Annotated Function |
|---|---|
| 10 | Sarcosine oxidase, alpha subunit |
| 11 | Hypothetical protein |
| 12 | Phage-like element PBSX protein xkdK |
| 13 | Phage-like element PBSX protein xkdM |
| 14 | Hypothetical protein |
| 15 | Hypothetical protein |
| 16 | Phage protein |
| 17 | Hypothetical protein |
| 18 | Phage-like element PBSX protein xkdQ |
| 19 | Ribosomal protein S4 and related proteins |
| 20 | Phage-like element PBSX protein xkdS |
| 21 | Hypothetical protein |
| 22 | Phage-like element PBSX protein xkdT |
| 23 | Tail fiber |
| 24 | Heat shock protein 90 |
| 25 | Hypothetical protein |
| 26 | Bacteriocin uviB precursor |
| 27 | N-acetylmuramoyl-L-alanine amidase (EC 3.5.1.28) |
| 28 | ABC transporter, permease protein |
| 29 | No hits |
| 30 | Transposase |
| 31 | DNA repair protein RadA |
| 32 | Transcriptional regulator |
| 33 | Hypothetical protein |
| 34 | Hypothetical protein |
| 35 | Thymidine kinase (EC 2.7.1.21) |
| 36 | Tryptophanyl-tRNA synthetase (EC 6.1.1.2) |
| 37 | CMP-binding factor |
| 38 | 3-isopropylmalate dehydratase large subunit (EC 4.2.1.33) |
| 39 | DNA ligase |
| 40 | Putative penicillin-binding protein |
| 41 | Signal transducer and activator of transcription 1 |
| 42 | Chemotaxis protein CHED |
| 43 | Gramicidin S synthetase I (EC 5.1.1.11) |
| 44 | ABC transporter ATP-binding protein |
| 45 | Putative ATP-dependent DNA helicase |
| 46 | DNA polymerase I |
| 47 | Hypothetical protein |
| 48 | Hypothetical protein |
| 49 | Phenylalanyl-tRNA synthetase beta chain |
| 50 | Terminase large subunit |
| 51 | Terminase small subunit |
| 52 | Hypothetical protein |
| 53 | CobT protein |
| 54 | Putative chromosome segregation protein, SMC ATPase superfamily |
| 55 | Deoxycytidylate deaminase (EC 3.5.4.12) |
| 56 | aceE; pyruvate dehydrogenase e1 component oxidoreductase protein |
| 57 | Hypothetical protein |
| 58 | Hypothetical protein |
| 59 | Aspartic acid-rich protein aspolin2 |
| 60 | CDEP |
| 61 | Nucleolin |
| 62 | Peptide ABC transporter, ATP-binding protein |
| 63 | GTP-binding protein SAR1 |
| 64 | gp56 dCTPase |
| 65 | Hypothetical protein |
| 66 | Homeobox-leucine zipper protein |
| 67 | DNA repair protein recN |
| CPAS-16 | |
| 1 | Developmentally regulated GTP-binding protein 1 |
| 2 | Presumed portal vertex protein |
| 3 | Ring-infected erythrocyte surface antigen |
| 4 | Hypothetical protein |
| 5 | Hypothetical protein |
| 6 | FKBP-type peptidyl-prolyl cis-trans isomerase (trigger factor) |
| 7 | Isocitrate dehydrogenase kinase/phosphatase |
| 8 | Phage-like element PBSX protein xkdH |
| 9 | High-affinity potassium transporter |
| 10 | Sarcosine oxidase, alpha subunit |
| 11 | Hypothetical protein |
| 12 | Phage-like element PBSX protein xkdK |
| 13 | Phage-like element PBSX protein xkdM |

TABLE 17-continued

Annotations of all predicted genes for each *C. perfringens*-specific bacteriophage genome

| Gene ID | Annotated Function |
|---|---|
| 14 | Hypothetical protein |
| 15 | Hypothetical protein |
| 16 | Phage protein |
| 17 | Hypothetical protein |
| 18 | Phage-like element PBSX protein xkdQ |
| 19 | Ribosomal protein S4 and related proteins |
| 20 | Phage-like element PBSX protein xkdS |
| 21 | Hypothetical protein |
| 22 | Phage-like element PBSX protein xkdT |
| 23 | Tail fiber |
| 24 | Heat shock protein 90 |
| 25 | Hypothetical protein |
| 26 | Bacteriocin uviB precursor |
| 27 | N-acetylmuramoyl-L-alanine amidase (EC 3.5.1.28) |
| 28 | Enterotoxin |
| 29 | Membrane protein |
| 30 | No hits |
| 31 | Thymidylate synthase (EC 2.1.1.45) |
| 32 | Heat shock protein (dnaJ-2) |
| 33 | Hypothetical protein |
| 34 | DNA polymerase I |
| 35 | DNA polymerase I |
| 36 | Putative ATP-dependent DNA helicase |
| 37 | ABC transporter ATP-binding protein |
| 38 | Terminase large subunit |
| 39 | Terminase small subunit |
| 40 | CobT protein |
| 41 | Putative chromosome segregation protein, SMC ATPase superfamily |
| 42 | Deoxycytidylate deaminase (EC 3.5.4.12) |
| 43 | aceE; pyruvate dehydrogenase e1 component oxidoreductase protein |
| 44 | Hypothetical protein |
| 45 | Hypothetical protein |
| 46 | Genomic DNA, chromosome 3, BAC clone: F1D9 |
| 47 | SWF/SNF family helicase |
| 48 | Aspartic acid-rich protein aspolin2 |
| 49 | CDEP |
| 50 | Nucleolin |
| 51 | Hypothetical protein |
| 52 | Putative reductase |
| 53 | Hypothetical protein |
| 54 | Hypothetical protein |
| 55 | Hypothetical protein |
| 56 | Tail fiber |
| 57 | gp56 dCTPase |
| 58 | Acetate kinase (EC 2.7.2.1) |
| 59 | GTP-binding protein SAR1 |
| 60 | Peptide ABC transporter, ATP-binding protein |
| 61 | Cytochrome b (EC 1.10.2.2) |
| 62 | Homeobox-leucine zipper protein |
| 63 | DNA repair protein recN |
| 64 | Transposase |
| 65 | DNA repair protein RadA |
| 66 | Exonuclease I |
| 67 | Transcriptional regulator |
| 68 | Hypothetical protein |
| 69 | Thymidine kinase (EC 2.7.1.21) |
| 70 | Tryptophanyl-tRNA synthetase (EC 6.1.1.2) |
| 71 | CMP-binding factor |
| 72 | 3-isopropylmalate dehydratase large subunit (EC 4.2.1.33) |
| 73 | DNA ligase |
| 74 | Putative penicillin-binding protein |
| 75 | Signal transducer and activator of transcription 1 |
| 76 | Chemotaxis protein CHED |
| 77 | Gramicidin S synthetase I (EC 5.1.1.11) |
| CPAS-15 | |
| 1 | Gramicidin S synthetase I (EC 5.1.1.11) |
| 2 | Chemotaxis protein CHED |
| 3 | Signal transducer and activator of transcription 1 |
| 4 | Putative penicillin-binding protein |
| 5 | DNA ligase |
| 6 | 3-isopropylmalate dehydratase large subunit (EC 4.2.1.33) |
| 7 | CMP-binding factor |

TABLE 17-continued

Annotations of all predicted genes for each *C. perfringens*-specific bacteriophage genome

| Gene ID | Annotated Function |
|---|---|
| 8 | Tryptophanyl-tRNA synthetase (EC 6.1.1.2) |
| 9 | Thymidine kinase (EC 2.7.1.21) |
| 10 | Hypothetical protein |
| 11 | Hypothetical protein |
| 12 | Transcriptional regulator |
| 13 | Exonuclease I |
| 14 | DNA repair protein RadA |
| 15 | Transposase |
| 16 | ABC transporter ATP-binding protein |
| 17 | Y56A3A.29a protein |
| 18 | DNA polymerase I |
| 19 | DNA polymerase I |
| 20 | Thymidylate synthase (EC 2.1.1.45) |
| 21 | Hypothetical protein |
| 22 | SWF/SNF family helicase |
| 23 | Aspartic acid-rich protein aspolin2 |
| 24 | CDEP |
| 25 | Hypothetical protein |
| 26 | Terminase large subunit |
| 27 | Terminase small subunit |
| 28 | CobT protein |
| 29 | Putative chromosome segregation protein, SMC ATPase superfamily |
| 30 | Deoxycytidylate deaminase (EC 3.5.4.12) |
| 31 | aceE; pyruvate dehydrogenase e1 component oxidoreductase protein |
| 32 | Hypothetical protein |
| 33 | Hypothetical protein |
| 34 | DNA repair protein recN |
| 35 | Homeobox-leucine zipper protein |
| 36 | Hypothetical protein |
| 37 | No hits |
| 38 | Hypothetical protein |
| 39 | N-acetylmuramoyl-L-alanine amidase (EC 3.5.1.28) |
| 40 | Bacteriocin uviB precursor |
| 41 | Hypothetical protein |
| 42 | Heat shock protein 90 |
| 43 | Tail fiber |
| 44 | PROBABLE SUCCINYL-COA SYNTHETASE BETA CHAIN PROTEIN |
| 45 | Phage-like element PBSX protein xkdT |
| 46 | Hypothetical protein |
| 47 | Phage-like element PBSX protein xkdS |
| 48 | Ribosomal protein S4 and related proteins |
| 49 | Phage-like element PBSX protein xkdQ |
| 50 | Hypothetical protein |
| 51 | Phage protein |
| 52 | Phage protein |
| 53 | Hypothetical protein |
| 54 | Hypothetical protein |
| 55 | Phage-like element PBSX protein xkdM |
| 56 | Phage-like element PBSX protein xkdK |
| 57 | Hypothetical protein |
| 58 | Sarcosine oxidase, alpha subunit |
| 59 | High-affinity potassium transporter |
| 60 | Phage-like element PBSX protein xkdH |
| 61 | Putative nodulation protein |
| 62 | Isocitrate dehydrogenase kinase/phosphatase |
| 63 | FKBP-type peptidyl-prolyl cis-trans isomerase (trigger factor) |
| 64 | Hypothetical protein |
| 65 | Hypothetical protein |
| 66 | Ring-infected erythrocyte surface antigen |
| 67 | Presumed portal vertex protein |
| 68 | GTP-binding protein SAR1 |
| 69 | Hypothetical protein |
| CPLV-42 | |
| 1 | Hypothetical protein |
| 2 | Ribosomal protein S4 and related proteins |
| 3 | Hypothetical protein |
| 4 | F14H3.11 protein |
| 5 | Myosin heavy chain, cardiac muscle beta isoform |
| 6 | Holin |
| 7 | N-acetylmuramoyl-L-alanine amidase (EC 3.5.1.28) |
| 8 | Developmentally regulated GTP-binding protein 1 |

TABLE 17-continued

Annotations of all predicted genes for each *C. perfringens*-specific bacteriophage genome

| Gene ID | Annotated Function |
|---|---|
| 9 | Hypothetical protein |
| 10 | DNA internalization-related competence protein ComEC/Rec2 |
| 11 | Phage-related protein |
| 12 | Antirepressor |
| 13 | Phage protein |
| 14 | Hypothetical protein |
| 15 | Excinuclease ABC subunit B |
| 16 | Putative oxidoreductase protein |
| 17 | DNA topoisomerase I (EC 5.99.1.2) |
| 18 | Imidazole glycerol phosphate synthase subunit hisF (EC 4.1.3.—) |
| 19 | Methyl-accepting chemotaxis protein |
| 20 | Hypothetical protein |
| 21 | Aminomethyltransferase (EC 2.1.2.10) |
| 22 | Hypothetical protein |
| 23 | Hypothetical protein |
| 24 | Hypothetical protein |
| 25 | Hypothetical protein |
| 26 | Hypothetical protein |
| 27 | Hypothetical protein |
| 28 | DNA polymerase III, subunit beta |
| 29 | Terminase large subunit |
| 30 | lin2585 |
| 31 | Portal protein |
| 32 | Genomic DNA, chromosome 3, BAC clone: F1D9 |
| 33 | Deoxyguanosinetriphosphate triphosphohydrolase (dgtP) |
| 34 | Virulence-associated protein E |
| 35 | Hypothetical protein |
| 36 | 3'-phosphoadenosine 5'-phosphosulfate sulfotransferase (PAPS reductase)/FAD synthetase and related enzymes, COG0175 |
| 37 | Phosphoadenosine phosphosulfate reductase (EC 1.8.4.8) |
| 38 | Hypothetical protein |
| 39 | Hypothetical protein |
| 40 | WRKY transcription factor 22 |
| 41 | D-threonine dehydrogenase |
| 42 | Hypothetical protein |
| 43 | Hypothetical protein |
| 44 | Transcriptional regulator |
| 45 | Single-strand binding protein |
| 46 | Hypothetical protein |
| 47 | Sensor histidine kinase |
| CPAS-12 | |
| 1 | Presumed portal vertex protein |
| 2 | Ring-infected erythrocyte surface antigen |
| 3 | Hypothetical protein |
| 4 | Hypothetical protein |
| 5 | FKBP-type peptidyl-prolyl cis-trans isomerase (trigger factor) |
| 6 | Isocitrate dehydrogenase kinase/phosphatase |
| 7 | Phage-like element PBSX protein xkdH |
| 8 | High-affinity potassium transporter |
| 9 | Sarcosine oxidase, alpha subunit |
| 10 | Hypothetical protein |
| 11 | Phage-like element PBSX protein xkdK |
| 12 | Phage-like element PBSX protein xkdM |
| 13 | Hypothetical protein |
| 14 | Hypothetical protein |
| 15 | Phage protein |
| 16 | Hypothetical protein |
| 17 | Phage-like element PBSX protein xkdQ |
| 18 | Ribosomal protein S4 and related proteins |
| 19 | Phage-like element PBSX protein xkdS |
| 20 | Hypothetical protein |
| 21 | Phage-like element PBSX protein xkdT |
| 22 | Tail fiber |
| 23 | Heat shock protein 90 |
| 24 | Hypothetical protein |
| 25 | Bacteriocin uviB precursor |
| 26 | N-acetylmuramoyl-L-alanine amidase (EC 3.5.1.28) |
| 27 | ABC transporter, permease protein |
| 28 | No hits |
| 29 | Gramicidin S synthetase I (EC 5.1.1.11) |
| 30 | Chemotaxis protein CHED |
| 31 | Signal transducer and activator of transcription 1 |
| 32 | Putative penicillin-binding protein |
| 33 | DNA ligase |
| 34 | 3-isopropylmalate dehydratase large subunit (EC 4.2.1.33) |
| 35 | CMP-binding factor |
| 36 | Tryptophanyl-tRNA synthetase (EC 6.1.1.2) |
| 37 | Thymidine kinase (EC 2.7.1.21) |
| 38 | Nucleolin |
| 39 | Transcriptional regulator |
| 40 | DNA repair protein RadA |
| 41 | Transposase |
| 42 | Hypothetical protein |
| 43 | Thymidylate synthase (EC 2.1.1.45) |
| 44 | Heat shock protein (dnaJ-2) |
| 45 | DNA polymerase I |
| 46 | Putative ATP-dependent DNA helicase |
| 47 | ABC transporter ATP-binding protein |
| 48 | Terminase large subunit |
| 49 | Terminase small subunit |
| 50 | CobT protein |
| 51 | Putative chromosome segregation protein, SMC ATPase superfamily |
| 52 | Deoxycytidylate deaminase (EC 3.5.4.12) |
| 53 | aceE; pyruvate dehydrogenase e1 component oxidoreductase protein |
| 54 | Hypothetical protein |
| 55 | Hypothetical protein |
| 56 | Genomic DNA, chromosome 3, BAC clone: F1D9 |
| 57 | SWF/SNF family helicase |
| 58 | Aspartic acid-rich protein aspolin2 |
| 59 | CDEP |
| 60 | Nucleolin |
| 61 | Alpha/beta hydrolase fold: Esterase/lipase/thioesterase family . . . |
| 62 | Normocyte-binding protein 1 |
| 63 | Hypothetical protein |
| 64 | DNA repair protein recN |
| 65 | Homeobox-leucine zipper protein |
| 66 | Hypothetical protein |
| 67 | gp56 dCTPase |

Example 5

Use of a Water-conditioning Agent in the Phage Cocktail

Phage cocktail INT-40 at a final concentration of $1\times10^7$ pfu/mL was placed into treated (containing 50 mM citrate-phosphate-thiosulfate (CPT) buffer, comprising about 40 mg sodium thiosulfate, 6.0 gm disodium phosphate (anhydrous), 1.1 gm citric acid (anhydrous) per liter of deionized water, pH 7.0 (added at a 1:10 ratio to water) and untreated (distilled water) solutions containing added bleach at the levels indicated in Table 18, and allowed to stand for one hour at room temperature. Samples were taken, and 10 microliters were spotted onto BHI agar medium containing lawns of *C. perfringens* ATCC 13124 and allowed to dry. Plates were incubated overnight at 37° C., and phage inactivation was scored by the absence of a lytic clearing zone visible on the bacterial lawn.

Results: The results in Table 1 demonstrated the thiosulfate-containing buffer was able to protect phage cocktail INT-401 against oxidation due to chlorine bleach exposure. This conditioning agent could therefore be applied to chlorinated water as a means to allow the phage cocktail to retain activity in a commercial poultry watering system.

TABLE 18

Water Conditioning Agent Allowing Protection of Phage Cocktail INT-401 in the presence of Hypochlorite

| Hypochlorite | Lysis Response vs. ATCC 13124 | |
|---|---|---|
| Concentration (ppm) | Conditioned Water | Unconditioned Water |
| 0 | ++ | ++ |
| 0.5 | ++ | + |
| 1 | ++ | + |
| 2 | + | − |
| 4 | + | − |
| 6 | + | − |

Lysis Response:
++ Clear Lysis
+ Partial Lysis
− No Lysis

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item. All ranges disclosed herein are inclusive and combinable.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated herein by reference in their entirety.

The invention claimed is:

1. The A purified bacteriophage preparation comprising CPAS-7 (accession number PTA-8479), CPAS-15 (accession number PTA-8480), CPAS-16 (accession number PTA-8481) and CPLV-42 (accession number PTA-8483) wherein each bacteriophage has lytic activity against at least five *C. perfringens* strains which cause necrotic enteritis in poultry.

2. The purified bacteriophage preparation of claim 1, wherein the at least five *C. perfringens* strains comprise ATCC strain 3624 and ATCC strain 9856.

3. The purified bacteriophage preparation of claim 1 wherein the *C. perfringens* strains comprise at least five of ATCC strain 25768, ATCC strain 3624, ATCC strain 9856, ATCC strain 3628, ATCC strain 13124, ATCC strain PTA-8495, NRRL strain B-50143, NRRL strain B-50144, NRRL strain B-50145, or a combination thereof.

4. The purified bacteriophage preparation of claim 1 wherein the preparation has lytic activity against ATCC strain 25768, ATCC strain 3624, ATCC strain 9856, ATCC strain 3628, ATCC strain 13124, ATCC strain PTA-8495, NRRL strain B-50143, NRRL strain B-50144, NRRL strain B-50145.

5. The purified bacteriophage preparation of claim 4, wherein the bacteriophage preparation is incapable of infecting at least ten strains of *E. coli, L. monocytogenes, S. enterica*, and *P. aeruginosa.*

6. The purified bacteriophage preparation of claim 1 comprising five or more *C. perfringens*-specific bacteriophage, wherein each bacteriophage has lytic activity against at least five *C. perfringens*strains.

7. The purified bacteriophage preparation of claim 6, comprising CPAS-12 (accession number PTA-8479), CPAS-15 (accession number PTA-8480), CPAS-16 (accession number PTA-481), CPLV-42 (accession number PTA-8483) and CPAS-7 (accession number PTA-8482 wherein each bacteriophage has lytic activity against at least five *C. perfringens* strains which cause necrotic enteritis in poultry.

8. The purified bacteriophage preparation of claim 7 wherein the at least five *C. perfringens* strains comprise ATCC strain 3624 and ATCC strain 9856.

9. The purified bacteriophage preparation of claim 7 wherein the *C. perfringens* strains comprise at least five of ATCC strain 25768, ATCC strain 3624, ATCC strain 9856, ATCC strain 3628, ATCC strain 13124, ATCC strain PTA-8495, NRRL strain B-50143, NRRL strain B-50144, NRRL strain B-50145, or a combination thereof.

10. The purified bacteriophage preparation of claim 7 wherein the preparation has lytic activity against ATCC strain 25768, ATCC strain 3624, ATCC strain 9856, ATCC strain 3628, ATCC strain 13124, ATCC strain PTA-8495, NRRL strain B-50143, NRRL strain B-50144, NRRL strain B-50145.

11. The purified bacteriophage preparation of claim 10, wherein the bacteriophage preparation is incapable of infecting at least ten strains of *E. coli, L. monocytogenes, S. enterica,* and *P. aeruginosa.*

12. The purified bacteriophage preparation of claim 1, wherein the bacteriophage preparation lyses greater than or equal to 85% of at least 40 screened *C. perfringens* strains, and wherein the bacteriophage preparation is incapable of infecting at least ten strains of *E. coli, L. monocytogenes, S. enterica*, and *P. aeruginosa.*

13. The purified bacteriophage preparation of claim 12, wherein the bacteriophage preparation lyses greater than or equal to 85% of at least 45 screened *C. perfringens* strains.

14. The purified bacteriophage preparation of claim 13, wherein each of the individual *C. perfringens*-specific bacteriophage lyses 15% to 90% of the screened *C. perfringens* strains.

15. The purified bacteriophage preparation of claim 1 further comprising a pharmaceutically acceptable excipient.

16. The purified bacteriophage preparation of claim 15, wherein the pharmaceutically acceptable excipient is a water-conditioning agent.

17. The purified bacteriophage preparation of claim 16, wherein the water-conditioning agent is a 50mM citrate-phosphate-thiosulfate buffer comprising about 40 mg sodium thiosulfate, 6.0 gm disodium phosphate (anhydrous), 1.1 gm citric acid (anhydrous) per liter of deionized water, pH 7.0, added at a 1:10 or greater ratio.

* * * * *